United States Patent
Inoue et al.

(10) Patent No.: US 9,187,570 B2
(45) Date of Patent: Nov. 17, 2015

(54) FUSION PROTEIN

(71) Applicant: AJINOMOTO CO., INC., Tokyo (JP)

(72) Inventors: Ippei Inoue, Kawasaki (JP); Ichiro Yamashita, Ikoma (JP); Bin Zheng, Ikoma (JP); Hisashi Yasueda, Kawasaki (JP); Yukiharu Uraoka, Ikoma (JP); Yasuaki Ishikawa, Ikoma (JP)

(73) Assignee: Ajinomoto Co., Ltd., Tokyo (JP)

( * ) Notice: Subject to any disclaimer, the term of this patent is extended or adjusted under 35 U.S.C. 154(b) by 154 days.

(21) Appl. No.: 13/923,974

(22) Filed: Jun. 21, 2013

(65) Prior Publication Data
US 2014/0045247 A1 Feb. 13, 2014

Related U.S. Application Data

(63) Continuation of application No. PCT/JP2011/079529, filed on Dec. 20, 2011.

(30) Foreign Application Priority Data

Dec. 22, 2010 (JP) ................................. 2010-286470
Aug. 8, 2011 (JP) ................................. 2011-173230

(51) Int. Cl.
C07K 19/00 (2006.01)
C07K 14/195 (2006.01)
C07K 7/06 (2006.01)
C07K 7/08 (2006.01)
C12N 15/62 (2006.01)

(52) U.S. Cl.
CPC . *C07K 19/00* (2013.01); *C07K 7/06* (2013.01); *C07K 7/08* (2013.01); *C07K 14/195* (2013.01); *C12N 15/62* (2013.01); *C07K 2319/00* (2013.01)

(58) Field of Classification Search
None
See application file for complete search history.

(56) References Cited

U.S. PATENT DOCUMENTS

| 7,462,462 | B2 | 12/2008 | Shiba et al. |
| 2006/0257931 | A1 | 11/2006 | Yamashita et al. |
| 2007/0112174 | A1 | 5/2007 | Shiba et al. |
| 2010/0029910 | A1 | 2/2010 | Shiba et al. |
| 2010/0040862 | A1 | 2/2010 | Shiba et al. |

FOREIGN PATENT DOCUMENTS

| JP | 2004-121154 | 4/2004 |
| JP | 2009-231224 | 10/2009 |
| JP | 2010-240794 | 10/2010 |
| WO | WO 2005/010031 | 2/2005 |
| WO | WO 2006/064639 | 6/2006 |
| WO | WO 2006/068250 | 6/2006 |
| WO | WO 2006/126595 | 11/2006 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Extended European Search Report issued on Aug. 21, 2014, in Patent Application No. 11851347.2.
Ichiro Yamashita, et al., Selective Nanoscale Positioning of Ferritin and Nanoparticles by Means of Target-Specific Peptides, Biological Nanomanipulation, Small, vol. 2, No. 10, XP055134031, 2006, pp. 1148-1152.
International Search Report in International Application No. PCT/JP2011/079529, dated Jan. 31, 2012.
I. Yamashita, et al., "Ferritin in the field of nanodevices", Biochem. Biophy. Acta, 2010, vol. 1800, pp. 846-857.
S. Wang, et al., "Peptides with selective affinity for carbon nanotubes", Nat. Mater., 2003, vol. 2, pp. 196-200.
S. Brown, "Metal-recognition by repeating polypeptides", Nat. Biotechnol., 1997, vol. 15, pp. 269-272.
K. Kjaergaard, et al., "Sequestration of Zinc Oxide by Fimbrial Designer Chelators", Appl. Enbiron. Microbiol., 2000, vol. 66, No. 1, pp. 10-14.
M. Dickerson, et al., "Identification of peptides that promote the rapid precipitation of Germania nanoparticle networks via use of a peptide display library", Chem. Commun., 2004, vol. 15, pp. 1776-1777.
C.E. Flynn, et al., "Synthesis and organization of nanoscale II-VI semiconductor materials using evolved peptide specificity and viral capsid assembly", J. Mater. Chem., 2003, vol. 13, pp. 2414-2421.
K. Sano, et al., "In aqua structuralization of a three-dimensional configuration using biomolecules", Nano Letters, 2007, vol. 7, No. 10, pp. 3200-3202.
K. Iwahori, et al., "Cadmium sulfide nanoparticle synthesis in dps protein from Listeria Innocua", Chem. Mater., 2007, vol. 19, pp. 3105-3111.
M. Pender, et al., "Peptide-mediated formation of single-wall carbon nanotube composites", Nano Letters, 2006, vol. 6, No. 1, pp. 40-44.
M. Fox, et al., "Heterogeneous Photocatalysis", Chem.. Rev., 1993, vol. 93, pp. 341-357.
X. Dang, et al., "Virus-templated self-assembled single-walled carbon nanotubes for highly efficient electron collection in photovoltaic devices", Nature Nanotechnology, 2011, vol. 6, pp. 377-384.
B. Fei, et al., "Solubilization, purification and functionalization of carbon nanotubes using polyoxometalate", Nanotechnology, 2006, vol. 17, pp. 1589-1593.
R. Tsukamoto, et al., "Improvement of $Co_3O_4$ nanoparticle synthesis in apoferritin cavity by outer surface PEGylation", Bull. Chem. Soc. Jpn., 2008, vol. 81, No. 12, pp. 1669-1674.

(Continued)

*Primary Examiner* — Christian Fronda
(74) *Attorney, Agent, or Firm* — Oblon, McClelland, Maier & Neustadt, L.L.P.

(57) ABSTRACT

The present invention provides means useful for making devices, materials and the like that are excellent in photocatalytic activity, electric property or the like. Specifically, the present invention provides a fusion protein comprising a polypeptide portion capable of forming a multimer having an internal cavity, and a first peptide portion capable of binding to a first target substance and a second peptide portion capable of binding to a second target substance; a multimer of the fusion protein; a complex comprising the multimer of the fusion protein; and the like.

13 Claims, No Drawings

(56) References Cited

OTHER PUBLICATIONS

R. Tsukamoto, et al., "Synthesis of $Co_3O_4$ nanoparticle using the cage-shaped protein, apoferritin", Bull. Chem. Soc. Jpn., 2005, vol. 78, pp. 2075-2081.
B. Zheng, et al., "Site-directed delivery of ferritin-encapsulated gold nanoparticles", Nanotechnology, 2010, vol. 21, No. 4, pp. 1-6.
T. Haikarainen, et al., "Dps-like proteins: structural and functional insights into a versatile protein family", Cell. Mol. Life Sci., 2010, vol. 67, No. 3, pp. 341-351.
I. Inoue, et al., "A novel bifunctional protein supramolecule for construction of carbon nanotube-titanium hybrid material", Chem. Commun., 2011, vol. 47, No. 47, pp. 12649-12651.
H. Yasueda, et al., "Green-Bio-Denshi Device (g-BED) Sosei eno Chosen", J. Soci. Biosci. and Bioeng., 2011, vol. 89, No. 11, pp. 670.
I. Inoue, et al., "Bio-Nano Process Gijutsuni yoru Hikari Shokubai Soshi Kochiku e Mukete", Dai 63 Kai Abstracts of the Annual Meeting of the Society for Biotechnology, 2011, pp. 12.
H. Yasueda, et al., "Nano-controlled fabrication of photoactive materials by cage-shaped mutant protein", Dai 72 Kai Extended Abstracts; The Japan Society of applied Physics, 2011, pp. 12-342.
K. Kaba, et al., "Genshiso Ti Hifuku SiO2 Kiban eno Ti Ninshiki Peptide Shushoku Ferritin no Kyuchaku Tokusei", Dai 30 Kai Hyomen Kagaku Gakujutsu Koenkai Yoshishu, Dai 51 Kai Annual symposium of the vacuum Society of Japan Yokoshu, 2010, pp. 147.
N. Matsukawa, et al., "Titanium Ninshiki Peptide Fuka Ferritin no Nijigen Kisokuka Hairetsu", Dai 55 Kai Extended Abstracts, Japan Society of Applied Physics and Related Societies, 2008, vol. 3, pp. 1278.
T. Hayashi, et al., "Critical amino acid residues for the specific binding of the Ti-recognizing recombinant ferritin with oxide surfaces of titanium and silicon", Langmuir, 2009, vol. 25, No. 18, pp. 10901-10906.
K. Sano, et al., "Endowing a ferritin-like cage protein with high affinity and selectivity for certain inorganic materials", Small, 2005, vol. 1, No. 8-9, pp. 826-832.
K. Kaba, et al., "Ti cho-usumaku-jo ni okeru Ti ninshiki peptide shushoku ferritin no kyuchaku kyodo", Dai 71 Kai Extended Abstracts, the Japan Society of Applied Physics, 2010, pp. 12-414.

* cited by examiner

FUSION PROTEIN

TECHNICAL FIELD

The present invention relates to a fusion protein. Specifically, the present invention relates to a fusion protein capable of forming a multimer having an internal cavity, a multimer of the fusion protein, and a complex comprising the multimer of the fusion protein, and the like.

BACKGROUND ART

Ferritin forms a 24-meric structure, and stores iron that is a metal essential for living organisms in an internal cavity formed by its structure. Ferritin-like proteins are ubiquitously present in organisms from animals and plants to microorganisms, and profoundly involved in homeostasis of an iron element in the living organisms and cells. One of the ferritin-like proteins that the microorganisms have is called Dps (DNA-binding protein from starved cells). Dps forms a 12-meric structure consisting of a monomer unit having a molecular weight of about 18 kDa, thereby forming a cage-like structure having an external diameter of 9 nm which has an internal cavity with a diameter of about 5 nm, and can store an iron molecule as an iron oxide nanoparticle in this internal cavity. Furthermore, it was shown that ferritin is able to artificially store the nanoparticles including oxides of metals such as beryllium, gallium, manganese, phosphorus, uranium, lead, cobalt, nickel, and chromium, and semiconductors/magnetic substances such as cadmium selenide, zinc sulfide, iron sulfide and cadmium sulfide, in addition to iron. Thus, ferritin is actively studied on its application in semiconductor material engineering and medical fields (Non-patent Literature 1)

In addition, peptides capable of binding to the inorganic material or the organic material are developed by screening using a phage for the purpose of making a complex of a biomaterial and an inorganic material or an organic material. For example, the peptides that recognize carbon nanotube (CNT) and carbon nanohorn (CNH) (Non-patent Literature 2, Patent Literatures 1 and 3), titanium oxide (Patent Literature 2), gold (Non-patent Literature 3), zinc oxide (Non-patent Literature 5), germanium oxide (Non-patent Literature 6), and zinc sulfide and cadmium sulfide (Non-patent Literature 7) and the like are known as such peptides.

Nanographite structures such as CNT and CNH that are carbon crystalline structures are expected to be applied to electronic materials, catalysis, optical materials, medical technology, and the like by constructing a complex with the other nanomaterial based on their electric properties and structures. Technology of constructing a nanocomplex by attaching the nanographite structure with metal nanoparticles using ferritin fused with a CNH binding peptide is reported (Non-patent Literature 2 and Patent Literature 3).

Titanium oxide generates an electron having a reduction capacity and a hole having an oxidation capacity on its surface by light energy when receiving the light. By taking advantage of its oxidation capacity and reduction capacity, titanium oxide is attempted to be applied to antimicrobial materials, deodorant materials, air cleaning materials, anti-stain materials, hydrogen generating catalysts, solar cells, and the like (Non-patent Literature 11). For example, when hydroxide ion is oxidized utilizing the oxidation capacity generated on the surface of titanium oxide by the light, radical having strong oxidation capacity can be generated. The radical can enhance biocidal effects, effects of decomposing odor substances such as acetaldehyde and ammonia, effects of decomposing harmful substances such as NOx and formaldehyde in air, and effects of decomposing dusts by its oxidation capacity. It is also attempted that water is electrolyzed utilizing the generated oxidation reduction capacities to produce oxygen and hydrogen and the hydrogen is utilized as clean energy. Titanium oxide can be utilized as the solar cell by isolating excited electrons generated in titanium oxide by light. Titanium oxide can be functioned as the solar cell by adsorbing a dye as an enhancer to the surface of the titanium oxide and isolating the excited electrons generated by irradiating the dye with light.

In order to enhance a performance of such materials utilizing the titanium oxide, it is conceivable to increase a surface area of the titanium oxide and enhance electric properties of the titanium oxide. Specifically, the increase of the surface area of the titanium oxide can increase total numbers of electrons having reduction capacity and holes having oxidation capacity which are generated by light energy, and a total number of dyes adsorbed to the surface. In addition, the enhancement of the electric properties can decrease a probability that electrons excited by light are bound again to holes. Thus, more electrons and oxidation capacity can be obtained.

To date, technology of laminating an oxide film and nanoparticles by arranging the nanoparticles on a silicon substrate, forming a titanium oxide film or a silicon oxide film on the nanoparticles, and arranging the nanoparticles on the oxide film, which technology utilizes a metal encapsulating protein, ferritin fused with titanium oxide, is known (Patent Literature 4). It is also reported that a protein encapsulating metal nanoparticles of cobalt or an iron oxide is oriented on a pattern depicted by titanium utilizing the metal encapsulating protein, ferritin fused with titanium oxide (Non-patent Literature 8).

Further, it is also reported that a CNT surface is coated with titanium oxide to change the electric property of CNT by using a polypeptide consisting of 35 amino acid residues in which a CNT-binding peptide was fused to a titanium oxide-binding peptide (Non-patent Literature 10). Technology of coating the carbon nanotube with titanium oxide using virus (Non-patent Literature 11) and technology of coating the carbon nanotube with titanium using polyoxometalate (Non-patent Literature 12) is also reported.

PRIOR ART REFERENCE

Patent Literature

Patent Literature 1: International Publication No. WO2006/068250.
Patent Literature 2: International Publication No. WO2005/010031.
Patent Literature 3: JP Publication No. 2004-121154.
Patent Literature 4: International Publication No. WO2006/126595.

Non-Patent Literature

Non-patent Literature 1: I. Yamashita et al., Biochem Biophys. Acta, 2010, vol. 1800, p. 846.
Non-patent Literature 2: S. Wang et al., Nat. Mater., 2003, vol. 2, p. 196.
Non-patent Literature 3: S. Brown, Nat. Biotechnol., 1997, vol. 15, p. 269.
Non-patent Literature 4: R. Tsukamoto et al., WSEAS Trans. Biol. Biomed., 2006, vol. 36, p. 443.
Non-patent Literature 5: K. Kjaergaard et al., Appl. Enbiron. Microbiol., 2000, vol. 66, p. 10.

Non-patent Literature 6: M. B. Dickerson et al., Chem. Commun., 2004, vol. 15, p. 1776.

Non-patent Literature 7: C. E. Flynn et al., J. Mater. Chem., 2003, vol. 13, p. 2414.

Non-patent Literature 8: K. Sano et al., Nano Lett., 2007, vol. 7, p. 3200.

Non-patent Literature 9: K. Iwahori et al., Chem. Mater., 2007, vol. 19, p. 3105.

Non-patent Literature 10: M. J. Pender et al., Nano Lett., 2006, vol. 6, No. 1, p. 44.

Non-patent Literature 11: M. A. Fox and M. T. Dulay, Chem. Rev., 1993, vol. 93, p. 341.

Non-patent Literature 12: Xiangnan Dang et al., Nature Nanotechnology, 2011, vol. 6, p. 377-384.

Non-patent Literature 13: Bin Fei et al., Nanotechnology, 2006, vol. 17, p. 1589-1593.

DISCLOSURE OF INVENTION

Problem to be Solved by the Invention

However, the aforementioned technologies are not sufficient for development of devices, materials and the like that are excellent in photocatalytic activity, electric properties or the like. Specifically, it was possible to coat CNT with titanium oxide to change electric natures by using a polypeptide in which the CNT-binding peptide was fused to the titanium oxide-binding peptide. However, it has been difficult to increase the surface area of titanium oxide to enhance the photocatalytic activity because the polypeptide mentioned above is small in size. It was also difficult to introduce metal nanoparticles inside a complex of CNT and titanium oxide to confer a new electric property.

Means for Solving Problem

As a result of an extensive study, the present inventors have found that a multimer of a fusion protein comprising a polypeptide portion capable of forming a multimer having an internal cavity, and a first peptide portion capable of binding to a first target substance and a second peptide portion capable of binding to a second target substance can be useful for producing the devices, materials and the like that are excellent in photocatalytic activity, electric properties or the like, and completed the present invention.

Accordingly, the present invention is as follows.

[1] A fusion protein comprising a polypeptide portion capable of forming a multimer having an internal cavity, and a first peptide portion capable of binding to a first target substance and a second peptide portion capable of binding to a second target substance.

[2] The fusion protein according to [1], wherein the first and second peptide portions are each a peptide portion capable of binding to a different target substance.

[3] The fusion protein according to [1] or [2], wherein a C-terminal part of the first peptide portion is fused to an N-terminal part of the polypeptide portion and an N-terminal part of the second peptide portion is fused to a C-terminal part of the polypeptide portion.

[4] The fusion protein according to [3], wherein the polypeptide portion capable of forming the multimer having the internal cavity is Dps.

[5] The fusion protein according to [4], wherein the Dps is a protein consisting of an amino acid sequence having 90% or more identity to an amino acid sequence represented by SEQ ID NO:4 or SEQ ID NO:29.

[6] The fusion protein according to any one of [1] to [5], wherein the first target substance and the second target substance are a metal material, a silicon material, or a carbon material.

[7] The fusion protein according to [6], wherein the metal material is a titanium material or a zinc material.

[8] The fusion protein according to [6], wherein the silicon material is silicon or an oxide of silicon.

[9] The fusion protein according to [6], wherein the carbon material is a carbon nanomaterial.

[10] The fusion protein according to [1], wherein the fusion protein is a protein consisting of an amino acid sequence having 90% or more amino acid sequence identity to an amino acid sequence represented by SEQ ID NO:2, SEQ ID NO:27, or SEQ ID NO:32.

[11] A multimer of a fusion protein,
wherein the multimer has an internal cavity,
wherein the fusion protein comprises a polypeptide portion capable of forming the multimer having the internal cavity, and a first peptide portion capable of binding to a first target substance and a second peptide portion capable of binding to a second target substance.

[12] The multimer according to claim 11, wherein the multimer contains a substance in the internal cavity.

[13] A complex comprising the multimer according to [11] or [12], and a first and second substances, wherein the first target substance is bound to the first peptide portion in the fusion protein and the second target substance is bound to the second peptide portion in the fusion protein.

[14] A polynucleotide that encodes the fusion protein according to any of [1] to [10].

[15] An expression vector comprising the polynucleotide according to [14].

[16] A transformant comprising the expression vector according to [15].

[17] The transformant according to [16], wherein the transformant is *Escherichia coli*.

Effect of the Invention

The fusion protein, the multimer, and the complex of the present invention are useful for the production of the novel devices having the enhanced electric properties and/or photocatalytic activity, and for the fields of medical treatments, biological researches and the like. For example, by using a fusion protein comprising a peptide portion capable of binding to a titanium oxide and a peptide portion capable of binding to a carbon nanotube, it becomes possible to provide antimicrobial materials, deodorant materials, air cleaning materials, anti-stain materials, hydrogen generating apparatuses, solar cells, semiconductors and the like.

BEST MODES FOR CARRYING OUT THE INVENTION

The present invention provides a fusion protein. The fusion protein of the present invention can comprise a polypeptide portion capable of forming a multimer having an internal cavity, and a first peptide portion capable of binding to a first target substance and a second peptide portion capable of binding to a second target substance.

The term "polypeptide portion capable of forming a multimer having an internal cavity" refers to a polypeptide portion having an ability to form a multimer having a space inside thereof by association of the polypeptide portions. Several proteins is known as such a polypeptide portion. Examples of such a polypeptide portion may include ferritin capable of forming a 24-meric structure having an internal cavity and a ferritin-like protein capable of forming a multimer having an internal cavity. Examples of the ferritin-like protein capable of forming the multimer having the internal cavity may include Dps capable of forming a 12-meric structure having an internal cavity. The polypeptide portion capable of forming the multimer having the internal cavity may be naturally occurring proteins derived from any organism such as microorganisms, plants and animals or mutants of the naturally occurring proteins. Hereinafter, the polypeptide portion capable of forming the multimer having the internal cavity may be simply referred to as the polypeptide portion.

In one embodiment, the polypeptide portion capable of forming the multimer having the internal cavity is Dps. The term "Dps (DNA-binding protein from starved cells)" as used herein refers to a protein capable of forming a 12-meric structure having an internal cavity, as described in BACKGROUND ART. The term "Dps" includes naturally occurring Dps or mutants thereof. For the mutants of the naturally occurring Dps, preferred are those exposing its N-terminal part and C-terminal part on the surface of the 12-meric structure upon formation of the 12-meric structure, as is similar to the naturally occurring Dps. Dps may be also referred to as NapA, bacterioferritin, Dlp or MrgA depending on a type of the microorganism from which Dps is derived. Subtypes such as DpsA, DpsB, Dps1 and Dps2 are also known for Dps (see, T. Haikarainen and A. C. Papageorgion, Cell. Mol. Life. Sci., 2010 vol. 67, p. 341). Therefore, the term "Dps" includes the proteins called by these other names.

The microorganism from which Dps is derived is not particularly limited as long as the microorganism produces Dps. Examples of the microorganism may include bacteria belonging to genera *Listeria, Staphylococcus, Bacillus, Streptococcus, Vibrio, Escherichia, Brucella, Borrelia, Mycobacterium, Campylobacter, Thermosynechococcus* and *Deinococcus*, and *Corynebacterium*.

Examples of the bacteria belonging to genus *Listeria* may include *Listeria innocua* and *Listeria monocytogenes*. Examples of the bacteria belonging to genus *Staphylococcus* may include *Staphylococcus aureus*. Examples of the bacteria belonging to genus *Bacillus* may include *Bacillus subtilis*. Examples of the bacteria belonging to genus *Streptococcus* may include *Streptococcus pyogenes* and *Streptococcus suis*. Examples of the bacteria belonging to genus *Vibrio* may include *Vibrio cholerae*. Examples of the bacteria belonging to genus *Escherichia* may include *Escherichia coli*. Examples of the bacteria belonging to genus *Brucella* may include *Brucella melitensis*. Examples of the bacteria belonging to genus *Borrelia* may include *Borrelia burgdorferi*. Examples of the bacteria belonging to genus *Mycobacterium* may include *Mycobacterium smegmetis*. Examples of the bacteria belonging to genus *Campylobacter* may include *Campylobacter jejuni*. Examples of the bacteria belonging to genus *Thermosynechococcus* may include *Thermosynechococcus elongates*. Examples of the bacteria belonging to genus *Deinococcus* may include *Deinococcus radiodurans*. Examples of the bacteria belonging to genus *Corynebacterium* may include *Corynebacterium glutamicum*.

In preferred embodiments, Dps may be a protein consisting of an amino acid sequence having 700 or more similarity to an amino acid sequence of Dps derived from *Listeria innocua* or *Escherichia coli*, or *Corynebacterium glutamicum*. The percent similarity of the amino acid sequence of Dps to the amino acid sequence of Dps derived from *Listeria innocua* or *Escherichia coli*, or *Corynebacterium glutamicum* can be preferably 75% or more, more preferably 80% or more, still more preferably 85% or more, and most preferably 90% or more, 95% or more, 96% or more, 97% or more, 98% or more, or 99% or more. Dps has five α-helical segments in its secondary structure (see, A. Ilari et al., Nat. Struct. Biol., 2000, Vol. 7, p. 38, R. A. Grant et al. Nat. Struct. Biol. 1998, Vol. 5, p. 294, and R.

R. Crichton et al., 2010, Vol. 1800, p. 706). In terms of retaining a function of Dps, it is important to keep the above secondary structure. Therefore, when the protein consisting of the amino acid sequence having 70% or more similarity to the amino acid sequence of Dps derived from *Listeria innocua* or *Escherichia coli*, or *Corynebacterium glutamicum* is prepared, a desired mutation can be introduced by a well-known mutagenesis method such as a site-directed mutagenesis so as to keep the above secondary structure. For Dps derived from *Listeria innocua* as an example, the relationships between positions of amino acid residues in the amino acid sequence represented by SEQ ID NO:4 and the above secondary structure are specifically described below from its N-terminal side. (i) The amino acid residues at positions 1 to 8 (an N-terminal region exposed on the surface of a 12-meric structure); (ii) the amino acid residues at positions 9 to 33 (α-helix); (iii) the amino acid residues at positions 39 to 66 (α-helix); (iv) the amino acid residues at positions 75 to 81 (α-helix); (v) the amino acid residue at positions 95 to 122 (α-helix); (vi) the amino acid residue at positions 126 to 149 (α-helix); and (vii) the amino acid residues at positions 150 to 156 (a C-terminal region exposed on the surface of a 12-meric structure). Here, among (i) to (vii) above, (ii) to (vi) can be important for retaining the ability to form the multimer having the internal cavity. For exposing the N-terminal part of Dps on the surface of the 12-meric structure, (i) and (ii), particularly (ii) can be important, since it is required that the α-helix adjacent to the N-terminal part of Dps faces outward the 12-meric structure. For exposing the C-terminal part of Dps on the surface of the 12-meric structure, (vi) and (vii), particularly (vi) can be important, since it is required that the α-helix adjacent to the C-terminal part of Dps faces outward the 12-meric structure. Therefore, conservative amino acid substitution is preferred when an amino acid residue present in the above important regions is mutated. On the other hand, any mutation may be introduced when an amino acid residue present in the regions other than the aforementioned important regions is mutated. A person skilled in the art can easily prepare the mutant of the naturally occurring Dps by introducing a desired mutation into naturally occurring Dps so as to retain its function based on these guidelines.

The position of the amino acid residue to which the mutation is to be introduced in the amino acid sequence is apparent to a person skilled in the art as described above. However, the mutant of naturally occurring Dps may be prepared further with reference to a sequence alignment. Specifically, a person skilled in the art can recognize correlation between structure and function because a person skilled in the art can 1) compare a plurality of amino acid sequences of Dps (e.g., the amino acid sequence represented by SEQ ID NO:4 and the amino acid sequence of other Dps), 2) demonstrate relatively conserved regions and relatively non-conserved regions, and then 3) predict regions capable of playing an important role for the function and regions incapable of playing an important role for the function from the relatively conserved regions and the relatively non-conserved regions, respectively. Therefore, a person skilled in the art can identify the position to which the mutation is to be introduced in the amino acid sequence of Dps by the aforementioned secondary structure alone, and also can identify the position of the amino acid residue to which the mutation is to be introduced in the amino acid sequence of Dps by combining the secondary structure information and the sequence alignment information.

In one embodiment, the protein consisting of the amino acid sequence having 70% or more similarity to the amino acid sequence of Dps derived from *Listeria innocua* or *Escherichia coli*, or *Corynebacterium glutamicum* may be a protein consisting of an amino acid sequence that comprises one or several mutations of amino acid residues (e.g., deletions, substitutions, additions, and insertions) in the amino acid sequence of Dps derived from *Listeria innocua* or *Escherichia coli*, or *Corynebacterium glutamicum*, and retaining the function of Dps. One or several mutations of the amino acid residues may be introduced into one region or a plurality of different regions in the amino acid sequence. For the mutation of the amino acid residues in Dps, the number represented by the term "one or several" is, for example, 1 to 50, preferably 1 to 30, more preferably 1 to 20, still more preferably 1 to 10, and particularly preferably 1, 2, 3, 4 or 5.

When the amino acid residue is mutated by substitution, the substitution of the amino acid residue may be the conservative substitution. The term "conservative substitution" as used herein refers to that a certain amino acid residue is substituted with an amino acid residue having a similar side chain. Families of the amino acid residues having the similar side chain are well-known in the art. Examples of such a family may include amino acids having a basic side chain (e.g., lysine, arginine, histidine), amino acids having an acidic side chain (e.g., aspartic acid, glutamic acid), amino acids having a non-charged polar side chain (e.g., glycine, asparagine, glutamine, serine, threonine, tyrosine, cysteine), amino acids having a nonpolar side chain (e.g., alanine, valine, leucine, isoleucine, proline, phenylalanine, methionine, tryptophan), amino acids having a branched side chain at position β (e.g., threonine, valine, isoleucine), amino acids having an aromatic side chain (e.g., tyrosine, phenylalanine, tryptophan, histidine), amino acids having a hydroxyl group (alcoholic, phenolic)-containing side chain (e.g., serine, threonine, tyrosine), and amino acids having a sulfur-containing side chain (e.g., cysteine, methionine). Preferably, the conservative substitution of the amino acids may be the substitution between aspartic acid and glutamic acid, the substitution among arginine, lysine and histidine, the substitution between tryptophan and phenylalanine, the substitution between phenylalanine and valine, the substitution among leucine, isoleucine and alanine, and the substitution between glycine and alanine.

In another embodiment, the protein consisting of the amino acid sequence having 70% or more similarity to the amino acid sequence of Dps derived from *Listeria innocua* or *Escherichia coli*, or *Corynebacterium glutamicum* may be a protein encoded by a polynucleotide that hybridizes under a stringent condition with a nucleotide sequence complementary to a nucleotide sequence represented by SEQ ID NO:3 or SEQ ID NO:28, and retains the function of Dps. The "stringent condition" refers to a condition where a so-called specific hybrid is formed whereas a non-specific hybrid is not formed. It is difficult to clearly quantify such a condition, but to cite a case, such a condition is a condition where polynucleotides having high homology (e.g., identity or similarity), for example, 70% or more, preferably 80% or more, more preferably 90% or more, still more preferably 95% or more and particularly preferably 98% or more homology are hybridized with each other and polynucleotides having the lower homology than that are not hybridized. Specifically, such a condition may include hybridization in 6×SSC (sodium chloride/sodium citrate) at about 45° C. followed by washing once or twice or more with 0.2×SSC and 0.1% SDS at 50 to 65° C.

In a certain embodiment, Dps may be a protein consisting of an amino acid sequence having 70% or more identity to the amino acid sequence of Dps derived from *Listeria innocua* or *Escherichia coli*, or *Corynebacterium glutamicum*. The percent identity of the amino acid sequences of Dps may be preferably 75% or more, more preferably 80% or more, still more preferably 85% or more, most preferably 90% or more, 95% or more, 96% or more, 97% or more, 98% or more, or 99% or more.

In a still certain embodiment, Dps may be a protein consisting of, or comprising an amino acid sequence having 90% or more identity to the amino acid sequence represented by SEQ ID NO:4 or SEQ ID NO:29. The percent identity of the amino acid sequence of the fusion protein of the present invention to the amino acid sequence represented by SEQ ID NO:4 or SEQ ID NO:29 may be preferably 95% or more, more preferably 96% or more, still more preferably 97% or more, particularly preferably 98% or more, or 99% or more.

The homology (e.g., identity or similarity) of the amino acid sequences and the nucleotide sequences can be determined, for example, using the algorithm BLAST (Pro. Natl. Acad. Sci. USA, 90, 5873 (1993)) by Karlin and Altschul or FASTA (Methods Enzymol., 183, 63 (1990)) by Pearson. The programs referred to as BLASTP and BLASTN were developed based on this algorithm BLAST (see http://www.ncbi.nlm.nih.gov). Thus, the homology of the amino acid sequences and the nucleotide sequences may be calculated using these programs with default setting. Also, for example, a numerical value obtained by calculating the similarity as a percentage at a setting of "unit size to compare=2" using the full length of the polypeptide portion encoded in ORF using software GENETYX Ver. 7.0.9 from Genetyx Corporation employing Lipman-Pearson method may be used as the homology of the amino acid sequences. The lowest value among the values derived from these calculations may be employed as the homology of the nucleotide sequences and the amino acid sequences.

The terms "first peptide portion capable of binding to a first target substance" and "second peptide portion capable of binding to a second target substance" refer to a portion that has a peptide having an affinity to any target substance and can bind to the target substance. The first peptide portion and the second peptide portion may be the same or different from each other. Since various peptides having the affinity to the target substance are known, a portion having such a peptide can be used as the peptide portion in the present invention. Hereinafter, the first peptide portion and the second peptide portion may be simply referred to as the peptide portion capable of binding to the target substance. The expression "the peptide portion capable of binding to the target substance" is an expression including the terms "the first peptide portion capable of binding to the first target substance" and "the second peptide portion capable of binding to the second target substance", and thus, these expressions are interchangeably used. The peptide portion capable of binding to the target substance may have only one peptide having the affinity to any target substance or may have a plurality of same or different peptides (e.g., several such as 2, 3, 4, 5, or 6) having the affinity to any target substance. For example, when the peptide portion capable of binding to the target substance has a plurality of different peptides having the affinity to any target substance, P1R5 peptide (SSKKSGSYSGSKG-SKRRILGGGGHSSYWYAFNNKT [SEQ ID NO:21]) that is a fusion peptide of P1 peptide capable of binding to a carbon nanomaterial (SEQ ID NO:13) and R5 peptide capable of binding to a titanium material or a silicon material (SEQ ID NO:15) can be used as the peptide portion (see, e.g., M. J. Pender et al., Nano Lett., 2006, vol. 6, No. 1, p. 40-44). When the peptide portion capable of binding to the target substance has a plurality of peptides as above, the plurality of peptides can be fused in any order in the peptide portion. The fusion can be accomplished via an amide bond. The fusion can be accomplished directly via the amide bond or via the amide bond through a peptide (a peptide linker) consisting of one amino acid residue (e.g., methionine) or several (e.g., 2 to 50, preferably 2 to 30, more preferably 2 to 20, still more preferably 2 to 15 or 2 to 10, and most preferably 2, 3, 4, or 5) amino acid residues. Since various peptide linkers are known, such a peptide linker can also be used in the present invention.

Examples of the target substance (or the first or second target substance) may include inorganic materials and organic materials, or conductive materials, semiconductor materials, and magnetic materials. Specifically, such target substances may include metal materials, silicon materials, carbon materials, small compounds (e.g., biological substances such as porphyrin, radioactive substances, fluorescent substances, dyes, and medicines), polymers (e.g., hydrophobic organic polymers and conductive polymers such as poly(methyl methacrylate), polystyrene, polyethylene oxide, or poly(L-lactic acid)), proteins (e.g., oligopeptides or polypeptides), nucleic acids (DNA or RNA, or nucleosides, nucleotides, oligonucleotides or polynucleotides), carbohydrates (e.g., monosaccharides, oligosaccharides or polysaccharides), and lipids.

Examples of the metal materials may include metals and metal compounds. Examples of the metal may include titanium, chromium, zinc, lead, manganese, calcium, copper, calcium, germanium, aluminium, gallium, cadmium, iron, cobalt, gold, silver, platinum, palladium, hafnium, and tellurium. Examples of the metal compounds may include oxide, sulfide, carbonate, arsenide, chloride, fluoride and iodide of the metals, and intermetallic compounds. Oxide of the metal may include various oxides. Describing such an oxide using the oxide of titanium as one example, examples of the oxide of titanium may include titanium monoxide (CAS No. 12137-20-1), titanium dioxide (CAS No. 13463-67-7), titanium dioxide (anatase, CAS No. 1317-70-0), titanium dioxide (rutile, CAS No. 1317-80-2), and titanium trioxide (CAS No. 1344-54-3). More specifically, the metal compounds may include oxides of titanium as described above, chromium oxide, zinc oxide, lead oxide, manganese oxide, zeolite, calcium carbonate, copper oxide, manganese-calcium oxide, germanium oxide, aluminium oxide, hafnium oxide, lead titanium zirconate, gallium arsenide, zinc sulfide, lead sulfide, cadmium sulfide, iron platinum, cobalt platinum, and cadmium tellurium.

Examples of the silicon materials may include silicon and silicon compounds. Examples of the silicon compounds may include oxides of silicon (e.g., silicon monoxide (SiO), silicon dioxide ($SiO_2$)), silicon carbide (SiC), silane ($SiH_4$), and silicone rubbers.

Examples of the carbon materials may include carbon nanomaterials (e.g., carbon nanotube (CNT), carbon nanohorn (CNH)), fullerene (C60), graphene sheet, and graphite.

The peptide portion capable of binding to the target substance is not particularly limited as long as it has an affinity to the target substance as described above. Various peptides having the affinity to the target substance is known and developed. For example, the peptide capable of binding to the inorganic material or the organic material is developed by a technique such as screening using a phage for the purpose of making a complex of the biomaterial and the inorganic material or the organic material. Examples of the peptides developed by such a technique may include peptides capable of binding to the metal materials such as titanium, oxides of titanium and silver (K. Sano et al., Langmuir, 2004, vol. 21, p. 3090, International Publication No. WO2005/010031), gold (S. Brown, Nat. Biotechnol., 1997, vol. 15, p. 269), zinc oxide (K. Kjaergaard et al., Appl. Environ. Microbiol., 2000, vol. 66, p. 10, and Umetsu et al., Adv. Mater., 17, 2571-2575 (2005)), germanium oxide (M. B. Dickerson et al., Chem. Commun., 2004, vol. 15, p. 1776), and zinc sulfide and cadmium sulfide (C. E. Flynn et al., J. Mater. Chem., 2003, vol. 13, p. 2414); peptides capable of binding to the silicon materials such as silicon and oxides of silicon (H. Chen et al., Anal. Chem., 2006, vol. 78, p. 4872, M. J. Pender et al., Nano Lett., 2006, vol. 6, No. 1, p. 40-44, and K. Sano et al., Langmuir, 2004, vol. 21, p. 3090, and International Publication No. WO2005/010031); peptides capable of binding to the carbon materials such as carbon nanotube (CNT) and carbon nanohorn (CNH) (S. Wang et al., Nat. Mater., 2003, vol. 2, p. 196. and JP Publication No. 2004-121154); and peptides capable of binding to the polymers such as hydrophobic organic polymers (JP Publication No. 2008-133194). Therefore, such a peptide can also be used as the peptide portion capable of binding to the target substance in the present invention.

It is known that the peptide capable of binding to the metal is able to have an action for mineralization of the metal, and the peptide capable of binding to the metal compound is able to have an action for mineralization of the metal compound (K. Sano et al., Langmuir, 2004, vol. 21, p. 3090, and M. Umetsu et al., Adv. Mater., 2005, vol. 17, p. 2571). Therefore, when a peptide capable of binding to the metal material (metal or metal compound) is used as the peptide capable of binding to the target substance, the peptide capable of binding to the metal material can have such an action for the mineralization.

The fusion of the polypeptide portion and the first and second peptide portions can be accomplished via amide bonds. The fusion can be accomplished directly via the amide bond or via the amide bond through a peptide (a peptide linker) consisting of one amino acid residue (e.g., methionine) or several (e.g., 2 to 50, preferably 2 to 30, more preferably 2 to 20, still more preferably 2 to 15 or 2 to 10, and most preferably 2, 3, 4, or 5) amino acid residues. Since various peptide linkers are known, such a peptide linker can also be used in the present invention.

The order of fusing the polypeptide portion and the first and second peptide portions in the fusion protein of the present invention is not particularly limited, 1) the N-terminal part and the C-terminal part of the polypeptide portion may be fused to the C-terminal part and the N-terminal part (or the N-terminal part and the C-terminal part) of the first and second peptide portions, respectively, or 2) the N-terminal part of the polypeptide portion may be fused to the C-terminal part of the first peptide portion and the N-terminal part of the first peptide portion may further be fused to the C-terminal part of the second peptide portion, or 3) the C-terminal part of the polypeptide portion may be fused to the N-terminal part of the first peptide portion and the C-terminal part of the first peptide portion may further be fused to the N-terminal part of the second peptide portion. For example, when ferritin is used as the polypeptide portion, ferritin is preferably fused in the order of 2) above, since the N-terminal part of ferritin is exposed on the surface of the multimer whereas the C-terminal part is not exposed on the surface. On the other hand, when Dps is used as the polypeptide portion, Dps may be fused in any of the orders of 1) to 3) above, since both the N-terminal part and the C-terminal part of Dps can be exposed on the surface of the multimer.

In preferred embodiments, the fusion protein of the present invention can have the first peptide portion and the second peptide portion (one or plurality, respectively) on an N-terminal side and on a C-terminal side of the polypeptide portion, respectively. In other words, the C-terminal part of the first peptide portion is fused to the N-terminal part of the polypeptide portion and the N-terminal part of the second peptide portion is fused to the C-terminal part of the polypeptide portion.

The first peptide portion can be designed so as to have methionine encoded by a translation initiation codon or a portion including methionine at its N-terminus on the N-terminal side of the first peptide portion. The translation of the fusion protein of the present invention can be facilitated by such a design. The peptide portion including methionine at the N-terminus may be a peptide consisting of several (e.g., 2 to 50, preferably 2 to 30, more preferably 2 to 20, still more preferably 2 to 15 or 2 to 10, and most preferably 2, 3, 4, or 5) amino acid residues.

In preferred embodiments, the first peptide portion and the second peptide portion in the fusion protein of the present invention can bind to the different target substance. Examples of a combination of the target substances to which the first peptide portion and the second peptide portion are bound may include a combination of the inorganic material and the organic material, a combination of two inorganic materials, and a combination of two organic materials. More specifically, such combinations may include a combination of the metal material and the silicon material, a combination of the metal material and the carbon material, a combination of the silicon material and the carbon material, a combination of two metal materials, a combination of two silicon materials, and a combination of two carbon materials. Therefore, the combination of the first peptide portion and the second peptide portion may be a combination of the peptide portions capable of binding to the target substances described above.

In still preferred embodiments, one of the first and second peptide portions may bind to the carbon material and the other may bind to the metal material or the silicon material in the fusion protein of the present invention. In other words, the fusion protein of the present invention has a peptide portion capable of binding to the carbon material as the first peptide portion and has a peptide portion capable of binding to the metal material or the silicon material as the second peptide portion, or alternatively, has the peptide portion capable of binding to the metal material or the silicon material as the first peptide portion and has the peptide portion capable of binding to the carbon material as the second peptide portion.

For the peptide portion capable of binding to the carbon material, a peptide portion capable of binding to a carbon nanomaterial such as carbon nanotube (CNT) or carbon nanohorn (CNH) is preferred. Examples of such a peptide may include DYFSSPYYEQLF (SEQ ID NO:6) disclosed in Examples described later and JP Publication No. 2004-121154, HSSYWYAFNNKT (SEQ ID NO:13) disclosed in M. J. Pender et al., Nano Lett., 2006, vol. 6, No. 1, p. 40-44, and YDPFHII (SEQ ID NO:14) disclosed in JP Publication No. 2004-121154, or mutant peptides thereof (e.g., mutation such as conservative substitution for 1, 2, 3, 4 or 5 amino acid residues), or peptides having one or a plurality of such amino acid sequences.

For the peptide portion capable of binding to the metal material, a peptide portion capable of binding to a titanium material such as titanium or a titanium compound (e.g., a titanium oxide), and a peptide portion capable of binding to a zinc material such as zinc or a zinc compound (e.g., a zinc oxide) are preferred. Examples of the peptide portion capable of binding to the titanium material may include RKLPDA (SEQ ID NO:8) disclosed in Examples described later and International Publication No. WO2006/126595, SSKKSGSYSGSKGSKRRIL (SEQ ID NO:15) disclosed in M. J. Pender et al., Nano Lett., 2006, vol. 6, No. 1, p. 40-44, and RKLPDAPGMHTW (SEQ ID NO:16) and RALPDA (SEQ ID NO:17) disclosed in International Publication No. WO2006/126595, or mutant peptides thereof (e.g., mutation by conservative substitution of 1, 2, 3, 4 or 5 amino acid residues), or peptides having one or several such an amino acid sequence. Examples of the peptide portion capable of binding to the zinc material may include EAHVMHKVAPRPGGGSC (SEQ ID NO:30) disclosed in Example described later and Umetsu et al., Adv. Mater., 17, 2571-2575 (2005), or mutant peptides thereof (e.g., mutation such as conservative substitution for 1, 2, 3, 4 or 5 amino acid residues), or peptides having one or a plurality of such amino acid sequences.

For the peptide portion capable of binding to the silicon material, a peptide portion capable of binding to silicon or a silicon compound (e.g., an oxide of silicon) is preferred. Examples of such a peptide portion may include RKLPDA (SEQ ID NO:8) disclosed in Examples described later and International Publication No. WO2006/126595, SSKKSGSYSGSKGSKRRIL (SEQ ID NO:15) disclosed in M. J. Pender et al., Nano Lett., 2006, vol. 6, No. 1, p. 40-44, and MSPHPHPRHHHT (SEQ ID NO:18), TGRRRRLSCRLL (SEQ ID NO:19) and KPSHHHHHTGAN (SEQ ID NO:20) disclosed in International Publication No. WO2006/126595, or mutant peptides thereof (e.g., mutation such as conservative substitution for 1, 2, 3, 4 or 5 amino acid residues), or peptides having one or a plurality of such amino acid sequences.

In a specific embodiment, the fusion protein of the present invention may be a protein consisting of, or comprising an amino acid sequence having 90% or more identity to an amino acid sequence represented by SEQ ID NO:2, SEQ ID NO:27, or SEQ ID NO:32. The percent identity of the amino acid sequence of the fusion protein of the present invention to the amino acid sequence represented by SEQ ID NO:2, SEQ ID NO:27, or SEQ ID NO:32 may be preferably 95% or more, more preferably 96% or more, still more preferably 97% or more, and particularly preferably 98% or more or 99% or more.

The fusion protein of the present invention can be obtained from a transformant that expresses the fusion protein of the present invention. This transformant can be prepared by making an expression vector for the fusion protein of the present invention comprising a polynucleotide encoding the fusion protein of the present invention and then introducing this expression vector into a host. Examples of the host for expressing the fusion protein of the present invention may include various prokaryotic cells including bacteria belonging to genera *Escherichia* (*Escherichia coli*) and *Corynebacterium*, and *Bacillus subtilis*, and various eukaryotic cells including *Saccharomyces cerevisiae*, *Pichia stipitis* and *Aspergillus oryzae*.

*E. coli* as the host to be transformed will be described in detail. Examples of *E. coli* may include *E. coli* JM109 strain, DH5α strain, HB101 strain, and BL21 (DE3) strain that are subtypes of *E. coli* K12 strain. Methods of transformation and methods of selecting the transformant are described in Molecular Cloning: A Laboratory Manual, 3rd edition, Cold Spring Harbor Press (2001 Jan. 15). A method of making transformed *E. coli* and producing the fusion protein of the present invention using this will be specifically described below as one example.

For a promoter for expressing a DNA encoding the fusion protein of the present invention, a promoter generally used for the production of a heterologous protein in *E. coli* can be used. Examples of the promoter may include strong promoters such as a T7 promoter, a lac promoter, a trp promoter, a trc promoter, a tac promoter, a PR promoter and a PL promoter of lambda phage, and a T5 promoter. Examples of a vector may include pUC19, pUC18, pBR322, pHSG299, pHSG298, pHSG399, pHSG398, RSF1010, pACYC177, pACYC184, pMW119, pMW118, pMW219, pMW218, pQE30, and derivatives thereof.

A terminator that is a transcription termination sequence may be ligated downstream of a gene encoding the fusion protein of the present invention. Examples of such a terminator may include a T7 terminator, a fd phage terminator, a T4 terminator, a terminator of a tetracycline resistant gene, and a terminator of an *E. coli* trpA gene.

The vector for introducing a gene encoding the fusion protein of the present invention is preferably a so-called multicopy type, and may include a plasmid having a replication origin derived from ColE1, e.g., pUC-based plasmids and pBR322-based plasmids or derivatives thereof. Here, the "derivative" means a plasmid modified by substitution, deletion, insertion, addition, and/or inversion of a nucleotide(s). The "modification" referred to herein includes a mutation treatment by a mutating agent or irradiation with UV or the modification by natural mutation.

The vector preferably has a marker such as an ampicillin resistant gene for selecting the transformant. The expression vectors having the strong promoter are commercially available (e.g., pUC-based vectors manufactured by Takara Bio Inc., pPROK-based vectors manufactured by Clontech, and pKK233-2 manufactured by Clontech).

When *E. coli* is transformed with the obtained expression vector and the resulting *E. coli* is cultured, the fusion protein of the present invention is expressed.

Examples of culture media may include media such as M9-casamino acid medium and LB medium generally used for culturing *E. coli*. Conditions on cultivation, production induction and the like can be selected appropriately depending on the types of the marker in the vector used, the promoter, the host microorganism and the like.

The following method is available for recovering the fusion protein of the present invention. The fusion protein of the present invention can be obtained as a disrupted product or a lysed product by collecting the transformant that produces the fusion protein of the present invention followed by disrupting (e.g., sonication or homogenization) or lysing (e.g., a lysozyme treatment) the transformant. A purified protein, a crude purified protein, or a fraction containing the fusion protein of the present invention can be obtained by subjecting such a disrupted product or lysed product to a technique such as extraction, precipitation, filtration, or column chromatography.

The present invention also provides a polynucleotide encoding the fusion protein of the present invention and an expression vector comprising the polynucleotide and a transformant comprising the expression vector, as described above, which can be used for preparing the fusion protein of the present invention.

The polynucleotide of the present invention can comprise a polynucleotide portion encoding the polypeptide portion capable of forming the multimer having the internal cavity, and a polynucleotide portion encoding the first peptide portion capable of binding to the first target substance, and a polynucleotide portion encoding the second peptide portion capable of binding to the second target substance. The polynucleotide of the present invention can be specified from various points based on the aforementioned descriptions on the fusion protein of the present invention, since it encodes the fusion protein of the present invention.

In a specific embodiment, the polynucleotide of the present invention may be a polynucleotide consisting of, or comprising a nucleotide sequence having 90% or more identity to a nucleotide sequence represented by SEQ ID NO:1, SEQ ID NO:26, or SEQ ID NO:31. The percent identity of the nucleotide sequence of the polynucleotide of the present invention to the nucleotide sequence represented by SEQ ID NO:1, SEQ ID NO:26, or SEQ ID NO:31 may be preferably 95% or more, more preferably 96% or more, still more preferably 97% or more, and particularly preferably 98% or more or 99% or more.

The present invention provides a multimer of the fusion protein. The multimer of the present invention can have the internal cavity. The fusion protein that composes the multimer of the present invention is as described above. The multimer of the present invention can be formed autonomously by expressing the fusion protein of the present invention. The number of monomer units that compose the multimer of the present invention can be determined by the type of the polypeptide portion in the fusion protein of the present invention. Preferably, the multimer of the present invention may be a 12-meric structure, since it may have Dps as the polypeptide portion capable of forming the multimer having the internal cavity.

The multimer of the present invention may be a homomultimer composed of a single fusion protein as the monomer unit or may be a heteromultimer composed of a plurality of different fusion proteins (e.g., 2, 3, 4, 5, or 6). In the multimer of the present invention, the polypeptide portion in the fusion protein that composes the multimer is preferably a single polypeptide portion in terms of forming the multimer, but the first peptide portion and the second peptide portion may be different in the fusion proteins that compose the multimer. For example, when the multimer of the present invention is composed of two types of the fusion proteins and the polypeptide portion in the fusion protein has the peptide portions fused on its N-terminal side and C-terminal side, respectively, examples of a combination of two types of the fusion proteins may include the followings:

(i) combination of the first peptide portion (a)—the polypeptide portion—the second peptide portion (b) and the first peptide portion (c)—the polypeptide portion—the second peptide portion (d);

(ii) combination of the first peptide portion (a)—the polypeptide portion—the second peptide portion (b) and the first peptide portion (a)—the polypeptide portion—the second peptide portion (c);

(iii) combination of the first peptide portion (a)—the polypeptide portion—the second peptide portion (b) and the first peptide portion (c)—the polypeptide portion—the second peptide portion (b);

(iv) combination of the first peptide portion (a)—the polypeptide portion—the second peptide portion (b) and the first peptide portion (c)—the polypeptide portion—the second peptide portion (a);

(v) combination of the first peptide portion (a)—the polypeptide portion—the second peptide portion (a) and the first peptide portion (b)—the polypeptide portion—the second peptide portion (c);

(vi) combination of the first peptide portion (a)—the polypeptide portion—the second peptide portion (b) and the first peptide portion (b)—the polypeptide portion—the second peptide portion (a);

(vii) combination of the first peptide portion (a)—the polypeptide portion—the second peptide portion (a) and the first peptide portion (a)—the polypeptide portion—the second peptide portion (b); and
(viii) combination of the first peptide portion (a)—the polypeptide portion—the second peptide portion (a) and the first peptide portion (b)—the polypeptide portion—the second peptide portion (a).

[wherein, (a) to (d) represent different peptide portions (e.g., peptide portions capable of binding to the different target substance). (i) is a manner utilizing four types of the peptide portions, (ii) to (v) are manners utilizing three types of the peptide portions, and (vi) to (viii) are manners utilizing two types of the peptide portions.]

Specifically, when the multimer of the present invention is composed of two types of the fusion proteins and at least a peptide portion capable of binding to the carbon material and a peptide portion capable of binding to the metal material (e.g., titanium material, zinc material) or the silicon material are used as the peptide portions, in terms of changing the electric properties of a device to be made using the multimer of the present invention, examples of the combination of two types of the fusion proteins may include the followings:

(i-1) combination of the peptide portion capable of binding to the carbon material—the polypeptide portion—the peptide portion capable of binding to the metal material or the silicon material and a peptide portion capable of binding to a first other material—a peptide portion capable of binding to a second other material;

(i-2) combination of the peptide portion capable of binding to the metal material or the silicon material—the polypeptide portion—the peptide portion capable of binding to the carbon material and the peptide portion capable of binding to the first other material—the polypeptide portion—the peptide portion capable of binding to the second other material;

(i-3) combination of the peptide portion capable of binding to the carbon material—the polypeptide portion—the peptide portion capable of binding to the first other material and the peptide portion capable of binding to the metal material or the silicon material—the polypeptide portion—the peptide portion capable of binding to the second other material;

(i-4) combination of the peptide portion capable of binding to the carbon material—the polypeptide portion—the peptide portion capable of binding to the first other material and the peptide portion capable of binding to the second other material—the polypeptide portion—the peptide portion capable of binding to the metal material or the silicon material;

(i-5) combination of the peptide portion capable of binding to the first other material—the polypeptide portion—the peptide portion capable of binding to the carbon material and the peptide portion capable of binding to the metal material or the silicon material—the polypeptide portion—the peptide portion capable of binding to the second other material (i-6) combination of the peptide portion capable of binding to the first other material—the polypeptide portion—the peptide portion capable of binding to the second other material and the peptide portion capable of binding to the metal material or the silicon material—the polypeptide portion—the peptide portion capable of binding to the carbon material;

(ii-1) combination of the peptide portion capable of binding to the carbon material—the polypeptide portion—the peptide portion capable of binding to the metal material or the silicon material and the peptide portion capable of binding to the carbon material—the polypeptide portion—the peptide portion capable of binding to the first other material;

(ii-2) combination of the peptide portion capable of binding to the carbon material—the polypeptide portion—the peptide portion capable of binding to the first other material and the peptide portion capable of binding to the carbon material—the polypeptide portion—the peptide portion capable of binding to the metal material or the silicon material;

(ii-3) combination of the peptide portion capable of binding to the metal material or the silicon material—the polypeptide portion—the peptide portion capable of binding to the carbon material and the peptide portion capable of binding to the metal material or the silicon material—the polypeptide portion—the peptide portion capable of binding to the first other material;

(ii-4) combination of the peptide portion capable of binding to the metal material or the silicon material—the polypeptide portion—the peptide portion capable of binding to the first other material and the peptide portion capable of binding to the metal material or the silicon material—the polypeptide portion—the peptide portion capable of binding to the carbon material;

(ii-5) combination of the peptide portion capable of binding to the first other material—the polypeptide portion—the peptide portion capable of binding to the metal material or the silicon material and the peptide portion capable of binding to the first other material—the polypeptide portion—the peptide portion capable of binding to the carbon material;

(ii-6) combination of the peptide portion capable of binding to the first other material—the polypeptide portion—the peptide portion capable of binding to the carbon material and the peptide portion capable of binding to the first other material—the polypeptide portion—the peptide portion capable of binding to the metal material or the silicon material;

(iii-1) combination of the peptide portion capable of binding to the carbon material—the polypeptide portion—the peptide portion capable of binding to the metal material or the silicon material and the peptide portion capable of binding to the first other material—the polypeptide portion—the peptide portion capable of binding to the metal material or the silicon material;

(iii-2) combination of the peptide portion capable of binding to the carbon material—the polypeptide portion—the peptide portion capable of binding to the first other material and the peptide portion capable of binding to the metal material or the silicon material—the polypeptide portion—the peptide portion capable of binding to the first other material;

(iii-3) combination of the peptide portion capable of binding to the metal material or the silicon material—the polypeptide portion—the peptide portion capable of binding to the carbon material and the peptide portion capable of binding to the first other material—the polypeptide portion—the peptide portion capable of binding to the carbon material;

(iii-4) combination of the peptide portion capable of binding to the metal material or the silicon material—the polypeptide portion—the peptide portion capable of binding to the first other material and the peptide portion capable of binding to the carbon material—the polypeptide portion—the peptide portion capable of binding to the first other material;

(iii-5) combination of the peptide portion capable of binding to the first other material—the polypeptide portion—the peptide portion capable of binding to the metal material or the silicon material and the peptide portion capable of binding to the carbon material—the polypeptide portion—the peptide portion capable of binding to the metal material or the silicon material;

(iii-6) combination of the peptide portion capable of binding to the first other material—the polypeptide portion—the peptide portion capable of binding to the carbon material and the peptide portion capable of binding to the metal material or the silicon material—the polypeptide portion—the peptide portion capable of binding to the carbon material;

(iv-1) combination of the peptide portion capable of binding to the carbon material—the polypeptide portion—the peptide portion capable of binding to the metal material or the silicon material and the peptide portion capable of binding to the first other material—the polypeptide portion—the peptide portion capable of binding to the carbon material;

(iv-2) combination of the peptide portion capable of binding to the carbon material—the polypeptide portion—the peptide portion capable of binding to the first other material and the peptide portion capable of binding to the metal material or the silicon material—the polypeptide portion—the peptide portion capable of binding to the carbon material;

(iv-3) combination of the peptide portion capable of binding to the metal material or the silicon material—the polypeptide portion—the peptide portion capable of binding to the carbon material and the peptide portion capable of binding to the first other material—the polypeptide portion—the peptide portion capable of binding to the metal material or the silicon material;

(iv-4) combination of the peptide portion capable of binding to the metal material or the silicon material—the polypeptide portion—the peptide portion capable of binding to the first other material and the peptide portion capable of binding to the carbon material—the polypeptide portion—the peptide portion capable of binding to the metal material or the silicon material;

(iv-5) combination of the peptide portion capable of binding to the first other material—the polypeptide portion—the peptide portion capable of binding to the metal material or the silicon material and the peptide portion capable of binding to the carbon material—the polypeptide portion—the peptide portion capable of binding to the first other material;

(iv-6) combination of the peptide portion capable of binding to the first other material—the polypeptide portion—the peptide portion capable of binding to the carbon material and the peptide portion capable of binding to the metal material or the silicon material—the polypeptide portion—the peptide portion capable of binding to the first other material;

(v-1) combination of the peptide portion capable of binding to the carbon material—the polypeptide portion—the peptide portion capable of binding to the carbon material and the peptide portion capable of binding to the metal material or the silicon material—the polypeptide portion—the peptide portion capable of binding to the first other material;

(v-2) combination of the peptide portion capable of binding to the carbon material—the polypeptide portion—the peptide portion capable of binding to the carbon material and the peptide portion capable of binding to the first other material—the polypeptide portion—the peptide portion capable of binding to the metal material or the silicon material;

(v-3) combination of the peptide portion capable of binding to the metal material or the silicon material—the polypeptide portion—the peptide portion capable of binding to the metal material or the silicon material and the peptide portion capable of binding to the carbon material—the polypeptide portion—the peptide portion capable of binding to the first other material;

(v-4) combination of the peptide portion capable of binding to the metal material or the silicon material—the polypeptide portion—the peptide portion capable of binding to the metal material or the silicon material and the peptide portion capable of binding to the first other material—the polypeptide portion—the peptide portion capable of binding to the carbon material;

(v-5) combination of the peptide portion capable of binding to the first other material—the polypeptide portion—the peptide portion capable of binding to the first other material and the peptide portion capable of binding to the metal material or the silicon material—the polypeptide portion—the peptide portion capable of binding to the carbon material;

(v-6) combination of the peptide portion capable of binding to the first other material—the polypeptide portion—the peptide portion capable of binding to the first other material and the peptide portion capable of binding to the carbon material—the polypeptide portion—the peptide portion capable of binding to the metal material or the silicon material;

(vi) combination of the peptide portion capable of binding to the carbon material—the polypeptide portion—the peptide portion capable of binding to the metal material or the silicon material and the peptide portion capable of binding to the metal material or the silicon material—the polypeptide portion—the peptide portion capable of binding to the carbon material;

(vii-1) combination of the peptide portion capable of binding to the carbon material—the polypeptide portion—the peptide portion capable of binding to the carbon material and the peptide portion capable of binding to the carbon material—the polypeptide portion—the peptide portion capable of binding to the metal material or the silicon material;

(vii-2) combination of the peptide portion capable of binding to the metal material or the silicon material—the polypeptide portion—the peptide portion capable of binding to the metal material or the silicon material and the peptide portion capable of binding to the metal material or the silicon material—the polypeptide portion—the peptide portion capable of binding to the carbon material;

(viii-1) combination of the peptide portion capable of binding to the carbon material—the polypeptide portion—the peptide portion capable of binding to the carbon material and the peptide portion capable of binding to the metal material or the silicon material—the polypeptide portion—the peptide portion capable of binding to the carbon material; and (viii-2) combination of the peptide portion capable of binding to the metal material or the silicon material—the polypeptide portion—the peptide portion capable of binding to the metal material or the silicon material and the peptide portion capable of binding to the carbon material—the polypeptide portion—the peptide portion capable of binding to the metal material or the silicon material.

The multimer composed of a plurality of different types of the fusion proteins can be obtained by, for example, introducing a plurality of vectors expressing the different types of the fusion proteins or a single vector expressing the different types of the fusion proteins (e.g., vector capable of expressing polycistronic mRNA) into a single host cell and then expressing the different types of the fusion proteins in the single host cell. Such a multimer can also be obtained by allowing a first monomer composed of a single fusion protein and a second monomer composed of a single fusion protein (different from the fusion protein that composes the first monomer) to coexist and be left stand in the same vehicle (e.g., buffer). The monomer of the fusion protein can be prepared by, for example, leaving stand the multimer of the present invention in buffer at low pH. For details, see, e.g., B. Zheng et al., Nanotechnology, 2010, vol. 21, p. 445602.

The multimer of the present invention may contain a substance in its internal cavity. The substance in a form of a complex or a particle (e.g., nanoparticle, magnetic particle) may be encapsulated in the multimer of the present invention. A person skilled in the art can appropriately select a substance that can be encapsulated in the multimer of the present invention by considering a size of the internal cavity of the multimer of the present invention, a charge property of the amino acid residues in regions involved in encapsulation of the substance in the multimer of the present invention (e.g., C-terminal region: see R. M. Kramer et al., 2004, J. Am. Chem. Soc., vol. 126, p. 13282), and the like. For example, when the multimer of the present invention has Dps as the polypeptide portion, Dps has an internal cavity of about 40 to 60 $nm^3$ (diameter: about 5 nm). Therefore, the size of the substance that can be encapsulated in such a multimer can be, for example, 60 $nm^3$ or less, preferably 40 $nm^3$ or less, more preferably 20 $nm^3$ or less, still more preferably 10 $nm^3$ or less, and most preferably 5 $nm^3$ or less. It is also reported that the encapsulation of the substance into the internal cavity of the multimer can further be facilitated by changing the charge property in the region that can be involved in the encapsulation of the substance in the multimer (e.g., type and number of amino acid residues having a side chain that can be charged positively or negatively) (see, e.g., R. M. Kramer et al., 2004, J. Am. Chem. Soc., vol. 126, p. 13282). Therefore, the multimer of the fusion protein having the region in which the charge property is changed can also be used in the present invention. Examples of the substance that can be encapsulated in the multimer of the present invention may include inorganic materials as is similar to the aforementioned target substances. Specifically, the substances that can be encapsulated in the multimer of the present invention may include the metal materials and the silicon materials as described above. More specifically, such a substance may include iron oxides, nickel, cobalt, manganese, phosphorus, uranium, beryllium, aluminium, cadmium sulfide, cadmium selenide, palladium, chromium, copper, silver, gadolium complex, platinum cobalt, silicon oxide, cobalt oxide, indium oxide, platinum, gold, gold sulfide, zinc selenide, and cadmium selenium.

The encapsulation of the substance in the internal cavity of the multimer of the present invention can be carried out by known methods. For example, it can be carried out in the same manner as in the method of encapsulating the substance in the internal cavity of the multimer of ferritin or a ferritin-like protein such as Dps (see, e.g., I. Yamashita et al., Chem., Lett., 2005. vol. 33, p. 1158). Specifically, the substance can be encapsulated in the internal cavity of the multimer of the present invention by allowing the multimer of the present invention (or fusion protein of the present invention) and the substance to be encapsulated to coexist in the buffer such as HEPES buffer and then leaving them stand at an appropriate temperature (e.g., 0 to 37° C.) (see also Example 3).

The multimer of the present invention may be provided as a set of a plurality of different types of the multimers containing a plurality (e.g., 2, 3, 4, 5 or 6) of different types of the substances when containing the substance in the internal cavity. For example, when the multimer of the present invention is provided as a set of two types of the multimers containing two types of the substances, such a set can be obtained by combining a first multimer encapsulating a first substance and a second multimer encapsulating a second substance (different from the first substance), which are each prepared separately. Highly diverse multimers of the present invention can be obtained by appropriately combining diversified patterns of the fusion proteins with diversified patterns of the substances to be encapsulated, as described above.

The present invention also provides a complex. The complex of the present invention can comprise the multimer of the present invention and the first and/or second target substance. In the complex of the present invention, the first target substance can bind to the first peptide portion in the fusion protein, and the second target substance can bind to the second peptide portion in the fusion protein. The target substances are as described above. The first and the second target substances are preferably different target substances. The target substance may bind to another substance or object. For example, the target substance may be fixed onto a solid phase (e.g., plates such as well plates, supports, substrates, elements, and devices). Therefore, the complex of the present invention may further comprise the other substance or object as long as it can comprise the multimer of the present invention and the first target substance and/or the second target substance.

A porous structure can be prepared by burning the complex of the present invention. The porous structure is described a porous structure in which a first empty hole has been formed in a site where the multimer of the present invention was present can be obtained by, for example, burning the complex of the present invention at temperature at which the protein can be extinguished. A second empty hole indicates an empty hole that can be produced in a process of the precipitation of the second target substance and/or the burning. A porous structure in which the first empty hole has been formed in the site where the multimer of the present invention was present and a third empty hole has been formed in a site where the first target substance was present can be obtained by burning the complex of the present invention at temperature at which both the protein and the first target substance (e.g., carbon material such as carbon nanotube) that composes an aggregate can be extinguished. When the substance (e.g., metal particle) was encapsulated in the internal cavity of the multimer that composes the complex of the present invention, the substance (e.g., metal particle) can be left in the first empty hole. When the substance (e.g., metal particle 36) was encapsulated in the internal cavity of the multimer that composes the complex of the present invention and this substance is melted, a film (e.g., metal film) composed of this substance can be formed inside the first empty hole. The porous structure thus produced is useful for the development of the devices, the materials and the like that are excellent in photocatalytic activity and electric properties. For example, the porous structure is useful as a material or a constituent for producing photoelectric conversion elements (e.g., solar cells such as dye sensitized solar cells), hydrogen generation elements, water cleaning materials, antimicrobial materials, and semiconductor memory elements.

The present invention will be described with reference to the following Examples, but the present invention is not limited by these Examples.

EXAMPLES

Example 1

Production of Strain for Expressing Fusion Protein CNHBP-Dps-TBP (CDT)

The metal-encapsulating protein Dps from *Listeria innocua*, an N-terminus of which is fused with a carbon nanohorn-binding protein (abbreviated as CNHBP and consisting of the amino acid sequence DYFSSPYYEQLF (SEQ ID NO:6); see International Publication No. WO2006/068250) and a C-terminus of which is fused with a titanium oxide-binding protein (abbreviated as TBP and consisting of the amino acid sequence RKLPDA (SEQ ID NO:8); see International Publication No. WO2005/010031) was constructed (abbreviated as CNHBP-Dps-TBP or CDT, SEQ ID NOS:1 and 2) by the following procedure.

First, synthesized DNAs (SEQ ID NO:9 and SEQ ID NO:10) was annealed by heating a mixed solution of the synthesized DNAs at 98° C. for 30 seconds and rapidly cooling it to 4° C. This DNA solution and pET20 carrying a Dps gene from *Listeria innocua* (see, K. Iwahori et al., Chem. Lett., 2007, vol. 19, p. 3105) were separately digested completely with a restriction enzyme NdeI. These DNA products were ligated with T4 DNA ligase (Takara Bio Inc., Japan) to obtain the plasmid pET20-CD carrying a gene encoding Dps, the N-terminus of which is fused with CNHBP (CNHBP-Dps, abbreviated as CD). Subsequently, PCR was carried out using pET20-CD as a template, and oligonucleotides consisting of the nucleotide sequences represented by SEQ ID NOS: 11 and 12. The resulting PCR product was purified using Wizard SV Gel and PCR Clean-Up System (Promega, USA), and digested with the restriction enzymes DpnI and BamHI. The PCR product digested with the restriction enzymes was self-ligated using the T4 DNA ligase (Promega, USA). *E. coli* JM109 (Takara Bio Inc., Japan) was transformed with the self-ligated PCR product to construct JM 109 possessing the expression plasmid (pET20-CDT) carrying the gene encoding Dps (CDT), the N-terminus of which was fused with the carbon nanohorn-binding peptide and the C-terminus of which was fused with the titanium-binding peptide. The plasmid pET20-CDT was purified from the transformant using Wizard Plus Miniprep System (Promega, USA). Finally, BL21 (DE3) (Invitrogen, USA) was transformed with pET20-CDT to make a strain BL21 (DE3)/pET20-CDT for expressing the protein. Meanwhile, a strain for expressing CD used for control experiments was produced similarly.

Example 2

Purification of Fusion Protein CDT

BL21 (DE3)/pET20-CDT were cultured in 5 mL of LB medium (containing 100 mg/L of ampicillin) at 37° C. Eighteen hours after starting the cultivation, the cultured medium was inoculated to 3 L of new LB medium (containing 100 mg/L of ampicillin) and cultured with shaking using BMS-10/05 (ABLE, Japan) at 37° C. for 24 hours. The resulting microbial cells were collected by centrifugation (5,000 rpm, 5 minutes), and stored at −80° C. A half (6 g) of the cryopreserved microbial cells was suspended in 40 mL of 50 mM Tris-HCl buffer (pH 8.0). Subsequently, the microbial cells were disrupted by giving an ultrasonic pulse (200 W, Duty 45%) to the suspension every one second for 12 minutes using Digital Sonifier 450 (Branson, USA). The solution was centrifuged at 15,000 rpm for 15 minutes (JA-20, Beckman Coulter, USA), and a supernatant fraction was collected. The collected solution was heated at 60° C. for 20 minutes, and rapidly cooled on ice after the heating. The cooled solution was centrifuged (JA-20) at 17,000 rpm for 10 minutes, and a supernatant (about 20 mL) was collected again. This solution was sterilized using a disc filter (Millex GP, 0.22 μm, Millipore, USA). And, this solution was ultrafiltrated and concentrated using Amicon-Ultra-15 (NMWL. 50000, Millipore, USA) until a liquid amount became 10 mL to obtain a protein solution.

Subsequently, a CDT fraction that was an objective protein was purified from the protein solution using gel filtration chromatography. Specifically, 10 mL of the protein solution was applied to HiPrep 26/60 Sephacryl S-300 High resolution column (GE Healthcare, USA) equilibrated with Tris-HCl buffer (50 mM Tris-HCl solution containing 150 mM NaCl, pH 8.0), and separated/purified at a flow rate of 1.4 mL/minute to collect fractions corresponding to CDT. The following experiments were carried out using the purified CDT. Concerning CD used for the control experiments, a gene was expressed in the same manner as in CDT, the microbial cells were collected and treated with heat. Subsequently, an NaCl solution was added at a final concentration of 0.5 M to a supernatant after treatment with heat. The resulting solution was centrifuged (JA-20) at 6,000 rpm for 5 minutes, a supernatant was discarded, and a pellet was suspended in 50 mM Tris-HCl buffer (pH 8.0). This manipulation was repeated three times to purify CD. The purification of Dps was carried out according to K. Iwahori et al., Chem. Mater., 2007, vol. 19, p. 3105.

Example 3

Encapsulation of Metal Particle by Fusion Protein CDT

In order to confirm that the CDT multimer can encapsulate a metal particle like the Dps multimer, an iron oxide nanoparticle was formed in an internal cavity of the CDT multimer. Specifically, 1 mL of HEPES buffer (80 mM HEPES/NaOH (pH 7.5), 0.5 mg/mL of CDT, 1 mM iron ammonium sulfate, each at final concentration) containing CDT was prepared and left stand at 4° C. for 3 hours. After leaving stand at cooling, the solution was centrifuged (15,000 rpm, 5 minutes), the protein included in the supernatant was stained with 3% phosphotungstic acid (PTA) or 1% gold glucose (Au-Glc) and observed under a transmission electron microscope (TEM, JEM2200-FS, 200 kV).

CDT after forming the iron oxide nanoparticle was stained with PTA and observed, and the iron oxide nanoparticle having a diameter of about 5 nm was formed in the internal cavity of the CDT multimer with an outer diameter of about 9 nm. Also, in the staining with Au-Glc, it could be observed that the iron oxide nanoparticle was formed in this internal cavity. On the other hand, CDT before forming the iron oxide nanoparticle was stained with PTA and observed under the electron microscope, and a globular protein alone having an outer diameter of about 9 nm was observed.

From the above results, it was confirmed that the CDT multimer could encapsulate the substance in its internal cavity.

Example 4

Confirmation of Binding Ability of CNHBP in CDT

An activity of the carbon nanohorn-binding peptide (CNHBP) fused to the N-terminus of CDT was examined. It is known that CNHBP recognizes not only the carbon nanohorn (CNH) but also the carbon nanotube (CNT) (see International Publication No. WO2006/068250). First, HEPES buffer containing CDT or Dps (20 mM HEPES/NaOH (pH7.5), 0.3 mg/mL of CDT or Dps, and 0.3 mg/mL CNT (Sigma-Aldrich, 519308, carbon nanotube, single walled) each at final concentration) was prepared. The ultrasonic pulse every one second (200 W, Duty 20%) was given to this solution for 5 minutes using Digital Sonifier 450 (Branson, USA). The ultrasonicated protein/CNT mixed solution was centrifuged (15,000 rpm, 5 minutes), and complexes of the protein and CNT contained in the supernatant were stained with 3% PTA and observed under the transmission electron microscope (JEM-2200FS, 200 kV).

In the solution containing CDT having CNHBP at its N-terminus, an appearance where CDT was bound to circumference of CNT could be observed. On the other hand, in the solution containing Dps having no peptide capable of recognizing CNT, no prominent binding between the protein and CNT could be observed.

From the above results, it was found that CNHBP presented on CDT retained an ability to bind to CNT.

Example 5

Confirmation of Binding Ability of TBP in CDT

Next, an activity of the titanium oxide-binding peptide (TBP) fused to the C-terminus of CDT was examined. It is known that TBP binds to titanium and titanium oxide, silver, and silicon and silicon oxide (see, International Publication No. WO2005/010031). This time, binding between CDT and titanium or silicon oxide was measured using quarts crystal microbalance measurement method (QCM) using a titanium sensor.

First, the surface of the titanium sensor was washed by placing 50 μL of a washing solution [in which 98% (w/v) sulfuric acid and 30% (w/v) hydrogen peroxide water were mixed at 3:1] on the titanium sensor for the measurement for one minute and then washing it out with water. After repeating this washing three times, the titanium sensor was attached to a main body (QCM934, SEIKO EG and G). A frequency value of the titanium sensor was stabilized by dropping 500 μL of TBS buffer (50 mM Tris-HCl, 150 mM NaCl, pH 8.0) on the sensor and leaving it stand at room temperature for 3 hours. Subsequently, 400 μL of the TBS buffer was removed, 400 μL of a protein solution (0.1 mg/mL) in which CDT or CD had been dissolved in the same TBS buffer was applied, and change of the frequency was measured. As a result, the greater change of the frequency was observed in the CDT solution than in the CD solution. That is, it was suggested that the protein was more abundantly bound to the titanium sensor in CDT having TBP than in CD. After the change of the frequency was stabilized, the sensor was washed with the TBS buffer to remove the proteins not bound to the sensor. Subsequently, an aqueous solution of tetramethyloxysilane (TEMOS, Shin-ETsu Silicone) that became silicon oxide by a dehydration condensation reaction was applied onto the sensor, and the change of the frequency was measured. The aqueous solution of TEMOS was prepared by mixing 143 μL of 1 mM HCl and 25 μL of TEMOS liquid well, leaving it stand at room temperature for 5 minutes, and then diluting it with the TBS buffer to 10 times. When the aqueous solution of TEMOS was applied onto the sensor, the frequency was reduced and mineralization of silicon oxide was observed. Subsequently, the sensor on which silicon oxide had been mineralized was washed with the TBS buffer, and then the protein solution was applied thereon. As a result, the frequency was reduced when the CDT solution was applied whereas the frequency was not reduced when the CD solution was applied. That is, it was suggested that CD having no TBP could not bind to silicon oxide whereas CDT having TBP could bind to silicon oxide.

From the above results, it was found that TBP presented on CDT retained an ability to bind to titanium oxide and silicon oxide.

Example 6

Homology Analysis of Amino Acid Sequences of Dps

Amino acid sequences of Dps derived from other microorganisms (identified by GenBank Accession Numbers shown in Table 1) were subjected to the analysis of homology to the amino acid sequences of Dps derived from *Listeria innocua* and *Escherichia coli*. The homology was analyzed using the genetic information analysis software Genetyx (Genetyx Corporation). Algorithm of this software was based on Lipman-Pearson method (Lipman, D. J. and Pearson, W. R. 1985. Rapid and sensitive protein similarity searches. Science 227: 1435-1441.) Results of analyzing the homology (identity and similarity) to the amino acid sequence of Dps derived from *Listeria innocua* are shown in Table 2. Results of analyzing the homology (identity and similarity) to the amino acid sequence of Dps derived from *Escherichia coli* are shown in Table 3. Comparisons of similarities to Dps derived to *Listeria innocua* and *Escherichia coli* are shown in Table 4.

TABLE 1

| Dps | GenBank Accession No. |
|---|---|
| *Listeria innocua* Dps | P80725 |
| *Listeria monocytogenes* Dps | Q8Y8G1 |
| *Staphylococcus aureus* Dps | ADC38290 |
| *Bacillus subtilis* 168 MrgA | P37960 |
| *Streptococcus pyogenes* Dpr | YP_001128164 |
| *Vibrio cholerae* O1 Dps | NP_229797 |
| *Escherichia coli* Dps | CAA49169 |
| *Streptococcus suis* Dpr | AAN47189 |
| *Brucella melitensis* Dps | NP_540897 |
| *Borrelia burgdorferi* NapA | ZP_03436602 |
| *Mycobacterium smegmatis* Dps | P0C558 |
| *Campylobacter jejuni* bacterioferritin | YP_001483008 |
| *Thermosynechococcus elongatus* DpsA | NP_681404 |
| *Deinococcus radiodurans* Dps | Q9RZN1 |
| *Bacteroides fragilis* Bacterioferritin | YP_212885 |

TABLE 2

| Amino acid sequence | Identity (%) | Similarity (%) |
|---|---|---|
| *Listeria innocua* Dps | 100 | 100 |
| *Listeria monocytogenes* Dps | 98.7 | 100 |
| *Staphylococcus Aureus* Dps | 43.5 | 84.4 |
| *Bacillus subtilis* 168 MrgA | 34.9 | 83.9 |
| *Streptococcus pyogenes* Dpr | 42.3 | 80.8 |
| *Vibrio cholerae* O1 Dps | 28.2 | 80.5 |
| *Escherichia coli* Dps | 26.5 | 78.9 |
| *Streptococcus suis* Dpr | 42.3 | 78.8 |
| *Brucella Melitensis* Dps | 23.5 | 77.1 |
| *Borrelia Burgdorferi* NapA | 27.1 | 72.9 |
| *Mycobacterium smegmatis* Dps | 24 | 71.4 |
| *Campylobacter jejuni* bacterioferritin | 29.5 | 71.1 |
| *Thermosynechococcus Elongatus* DpsA | 17 | 70.6 |
| *Deinococcus Radiodurans* Dps | 24 | 68.8 |
| *Bacteroides Fragilis* Bacterioferritin | 10.3 | 51.9 |

TABLE 3

| Amino acid sequence | Identity (%) | Similarity (%) |
| --- | --- | --- |
| *Escherichia coli* Dps | 100 | 100 |
| *Brucella Melitensis* Dps | 55.7 | 86.2 |
| *Listeria innocua* Dps | 26.5 | 78.9 |
| *Listeria monocytogenes* Dps | 25.9 | 78.9 |
| *Streptococcus pyogenes* Dpr | 25.3 | 76.5 |
| *Mycobacterium smegmatis* Dps | 34.8 | 74.8 |
| *Staphylococcus Aureus* Dps | 23.6 | 74.3 |
| *Bacillus subtilis* 168 MrgA | 20 | 74 |
| *Streptococcus suis* Dpr | 21.5 | 73 |
| *Vibrio cholerae* O1 Dps | 19 | 71.9 |
| *Campylobacter jejuni* bacterioferritin | 22 | 70.2 |
| *Deinococcus Radiodurans* Dps | 22.2 | 70.1 |
| *Borrelia Burgdorferi* NapA | 27 | 69.1 |
| *Thermosynechococcus Elongatus* DpsA | 20.4 | 62.9 |
| *Bacteroides Fragilis* Bacterioferritin | 11.7 | 50 |

TABLE 4

| Amino acid sequence | vs *Listeria* | vs *E. coli* |
| --- | --- | --- |
| *Listeria innocua* Dps | 100 | 78.9 |
| *Listeria monocytogenes* Dps | 100 | 78.9 |
| *Staphylococcus Aureus* Dps | 84.4 | 74.3 |
| *Bacillus subtilis* 168 MrgA | 83.9 | 74 |
| *Streptococcus pyogenes* Dpr | 80.8 | 76.5 |
| *Vibrio cholerae* O1 Dps | 80.5 | 71.9 |
| *Escherichia coli* Dps | 78.9 | 100 |
| *Streptococcus suis* Dpr | 78.8 | 73 |
| *Brucella Melitensis* Dps | 77.1 | 86.2 |
| *Borrelia Burgdorferi* NapA | 72.9 | 69.1 |
| *Mycobacterium smegmatis* Dps | 71.4 | 74.8 |
| *Campylobacter jejuni* bacterioferritin | 71.1 | 70.2 |
| *Thermosynechococcus Elongatus* DpsA | 70.6 | 62.9 |
| *Deinococcus Radiodurans* Dps | 68.8 | 70.1 |
| *Bacteroides Fragilis* Bacterioferritin | 51.9 | 50 |

Example 7

Measurement of Binding Rate Constant and Dissociation Rate Constant in Binding of Fusion Protein CDT to Target Substance (1) Production of Strain for Expressing DT In order to construct a metal-encapsulating protein Dps from *Listeria innocua*, and the C-terminus of which was fused with TBP (abbreviated as Dps-TBP or DT), PCR was carried out using pET20-CDT as a template DNA, and oligonucleotides consisting of the following nucleotide sequences as the primers.

```
                                    (SEQ ID NO: 22)
TTTCATATGTATATCTCCTTCTTAAAGTTAAAC
and
                                    (SEQ ID NO: 23)
TTTCATATGATGAAAACAATCAACTCAGTAG
```

The resulting PCR product was purified by Wizard SV Gel and PCR Clean-Up System (Promega, USA), and digested with restriction enzymes DpnI and NdeI. The PCR product digested with the restriction enzymes was self-ligated using the T4 DNA ligase (Promega, USA). *E. coli* JM109 (Takara Bio Inc., Japan) was transformed with the self-ligated PCR product to construct JM109 possessing an expression plasmid carrying the gene encoding DT (pET20-DT). The plasmid pET20-DT was purified from the transformant using Wizard Plus Minipreps System (Promega, USA). Finally, BL21 (DE3) (Invitrogen, USA) was transformed with pET20-DT to obtain a strain BL21 (DE3)/pET20-DT for expressing protein. DT was expressed in the same manner as in the case of CDT.

(2) Purification of CDT, CD and DT

In order to prepare the proteins for analyzing by QCM, BL21 (DE3)/pET20-CDT, and BL21 (DE3)/pET20-DT and BL21 (DE3)/pET20-CD were cultured in 1 mL of LB medium (containing 100 mg/mL of ampicillin) at 37° C., respectively. Eighteen hours after starting the cultivation, the resulting culture medium was inoculated to 100 mL of new LB medium (containing 100 mg/L of ampicillin) and cultured with shaking using a 500 mL flask at 37° C. for 24 hours. The resulting microbial cells were collected by centrifugation (6,000 rpm, 5 minutes), and suspended in 5 mL of 50 mM Tris-HCl buffer (pH 8.0). The microbial solution was sonicated to disrupt the microbial cells. The resulting solution was centrifuged at 6,000 rpm for 15 minutes and a supernatant fraction was collected. The collected solution was heated at 60° C. for 20 minutes and then rapidly cooled on ice. The cooled solution was centrifuged at 6,000 rpm for 15 minutes and a supernatant (about 5 mL) was collected again. This solution was sterilized using the disc filter (Millex GP. 0.22 μm, Millipore, USA). And, the solution was ultrafiltrated and concentrated using Amicon-Ultra-15 (NMWL. 50000, Millipore, USA), and the buffer in which the protein was dissolved was replaced with Tris-HCl salt buffer (50 mM Tris-HCl solution containing 150 mM NaCl, pH 8.0) to obtain 2.5 mL of a protein solution.

CDT, CD and DT were purified from the obtained protein solutions. First, gel filtration and anion exchange chromatography were used for the purification of CDT and DT. Specifically, 2.5 mL of the crude extraction solution was applied to HiPrep 26/60 Sephacryl S-300 High resolution column (GE healthcare, USA) equilibrated with Tris-HCl salt buffer (50 mM Tris-HCl solution containing 150 mM NaCl, pH 8.0), eluted at a flow rate of 1.4 mL/minute, and fractions corresponding to each protein were collected. Subsequently, each the protein solution obtained was ultrafiltrated and concentrated, and the buffer of the protein solution was replaced with 50 mM Tris-HCl buffer (pH 8.0). Then, 2.5 mL of this protein solution was applied to HiLoard 26/10 Q-Sepharose High Performance column (GE healthcare, USA) equilibrated with 50 mM Tris-HCl buffer (pH 8.0). The separation/purification was carried out at a flow rate of 4.0 mL/minute by making a concentration gradient of the salt from 0 mM to 500 mM NaCl in 50 mM Tris-HCl buffer (pH 8.0), and fractions corresponding to each the protein were collected. CD was purified by salting out.

(3) Measurement of Binding Rate Constant and Dissociation Rate Constant between CDT and CNT A binding rate constant and a dissociation rate constant between CDT and CNT were measured by QCM method. First, the surface of a gold sensor was washed by placing 50 μL of a washing solution [in which 98% (w/v) sulfuric acid and 30% (w/v) hydrogen peroxide water were mixed at 3:1] on the gold sensor for the measurement for 5 minutes and then washing it out with water. CNT (carbon nanotube, single-walled, 519308, Aldrich) confirmed to form a complex with the protein under the transmission electron microscope was mixed at a final concentration of 1 mg/L with a 1% SDS solution and the mixture was sonicated for 30 minutes. Subsequently, 2 μL of the resulting CNT solution was mounted on the gold electrode and naturally dried at room temperature. After the drying, the electrode was washed twice with water to wash out CNT that was not bound to the electrode. The resulting CNT sensor was further washed once with phosphate buffer A (50 mM potassium phosphate buffer containing 0.001% (w/v) Tween-20, pH 7.4). This CNT sensor was attached on the main body (Affinix, QNµ, Initium), and the frequency value of the sensor was stabilized by dropping the phosphate buffer A on the CNT sensor, which was then left stand for 30 minutes to one hour. After stabilizing the frequency value, 500 µL of a reaction solution containing CDT or CD was added at a final concentration of 0.5 mg/L to 10 mg/L, and the change of the frequency was measured. And supposing that the obtained change of the frequency follows the following relation, the binding rate constant kon and the dissociation rate constant koff between the protein and CNT were calculated using analysis software AQUA (Initium). Supposing that CDT and CD each formed a 12-meric structure, 246 kDa and 236 kDa for each molecular weight were used for the calculation.

$$S = Smax \times \{1-\exp(-kbos \times t)\}$$ [Mathematical formula 1]

kbos=koff+P×kon
Kd=koff/kon
S: Concentration of complex of protein and sensor (M)
P: Concentration of protein used for reaction (M)
kon: Binding rate constant ($M^{-1} \times sec^{-1}$)
koff: Dissociation rate constant ($sec^{-1}$)
t: Reaction time (sec)
Smax: Concentration of complex of protein and sensor (M) when reaction reached equilibration
Kd: Dissociation constant (M)

As a result, the relation between kbos and the protein concentration in CDT and CD was determined. Values of kon and koff of each protein, which could be obtained from a straight line plot are as shown in Table 5. Therefore, it was found that CDT could bind to CNT with the similar strength as that of CD. It was believed that their ability to bind to CNT depended on CNTBP.

TABLE 5

Binding rate constant and dissociation rate constant between CDT and CNT

| Type of protein | Kon ($M^{-1} \cdot sec^{-1}$) | koff ($sec^{-1}$) | Kd (nM) |
|---|---|---|---|
| CDT | $1.5 \times 10^5$ | $1.0 \times 10^{-3}$ | 6.6 |
| CD | $1.6 \times 10^5$ | $1.4 \times 10^{-3}$ | 8.9 |

(4) Measurement of Binding Rate Constant and Dissociation Rate Constant Between CDT and Titanium Oxide The binding rate constant and the dissociation rate constant between CDT and titanium oxide were measured by QCM method. A titanium oxide sensor manufactured by Inisium was used. First, a 1% SDS solution was placed on the titanium oxide sensor, the sensor was washed by pipetting, and the extra SDS solution was washed out five times with water. This washing was repeated twice. Further, the sensor was washed once with phosphate buffer B (50 mM phosphate buffer pH 7.0). This titanium oxide sensor was attached on the main body (Affinix, QNµ, Initium), and the frequency value of the sensor was stabilized by dropping the phosphate buffer B on the sensor and leaving it stand at room temperature for 30 minutes to one hour. After stabilizing the frequency value, 500 µL of a reaction solution containing CDT or CT was added at a final concentration of 0.5 mg/L to 10 mg/L, and the change of the frequency was measured. The binding rate constant kon and the dissociation rate constant koff between the protein and titanium oxide were calculated from the obtained change of the frequency using the analysis software AQUA (Initium) in the same manner as in the case of calculating the binding constant to CNT. Supposing that the DT formed the 12-meric structure, its molecular weight as 226 kDa was used for the calculation.

As a result, the relation between knob and the protein concentration in CDT and CD was as determined. The values of kon and koff calculated from a straight line plot were as shown in Table 6. Therefore, it was found that CDT could bind to titanium oxide with the similar strength as that of DT. It was believed that their ability to bind to titanium oxide depended on TBP. From Tables 5 and 6, it was found that CDT had the ability to bind to both CNT and titanium oxide.

TABLE 6

Binding rate constant and dissociation rate constant between CDT and titanium oxide

| Type of protein | kon ($M^{-1} \cdot sec^{-1}$) | koff ($sec^{-1}$) | Kd (nM) |
|---|---|---|---|
| CDT | $3.6 \times 10^5$ | $5.5 \times 10^{-3}$ | 15 |
| DT | $3.5 \times 10^5$ | $5.7 \times 10^{-3}$ | 17 |

Example 8

Preparation of Fusion Protein CcDT
(1) Production of Strain for Expressing CcDT

A mutant protein having the similar nature as that of CDT was constructed using Dps derived from *Corynebacterium glutamicum*. The results of analysis of the amino acid sequence of Dps derived from *Corynebacterium glutamicum* to the amino acid sequences of Dps derived from *Listeria innocua* and *Escherichia coli* (identity and similarity) are shown in Table 7.

TABLE 7

Comparison of homology

| Amino acid sequence | Identity (%) | Similarity (%) |
|---|---|---|
| vs *L. innocua* Dps | 20.9 | 69.3 |
| vs *E. coli* Dps | 37.7 | 74.7 |

First, PCR was carried out using genomic DNA from *Corynebacterium glutamicum* as the template, and oligonucleotides consisting of the following nucleotide sequences as the primers.

(SEQ ID NO: 24)
tttcatAtggactacttctcttctccgtactacgaacagctgtttATGGC

AAACTACACAGTC (SEQ ID NO: 25)
tttGAATTCttaCGCATCCGGAAGTTTGCGCATCTCTTGGATGTTTCCGT

C

The obtained PCR product was purified using Wizard SV Gel and PCR Clean-Up System (Promega, USA) and digested with the restriction enzymes NdeI and EcoRI. Meanwhile, the plasmid pET20b (Merck, Germany) was digested with the restriction enzymes NdeI and BamHI. The PCR product and the plasmid digested with the restriction enzymes were ligated using the T4 ligase (Promega, USA). *E. coli* JM109 (Takara Bio Inc., Japan) was transformed with the resulting DNA to construct JM109 possessing an expression plasmid (pET20-CcDT) carrying the gene encoding Dps derived from *Corynebacterium glutamicum*, the N-terminus of which was fused with the carbon nanohorn-binding peptide (CNHBP), and the C-terminus of which was fused with the titanium-binding peptide (TBP) (CcDT, SEQ ID NOS:26 and 27). The plasmid pET20-CcDT was purified from this transformant using Wizard Plus Minipreps System (Promega, USA). Finally, BL21 (DE3) (Invitrogen, USA) was transformed with pET20-CcDT to obtain the strain BL21 (DE3)/pET20-CcDT for expressing the protein.

(2) Purification of CcDT

In order to obtain the CcDT protein, BL21 (DE3)/pET20-CcDT was cultured in 1 mL of LB medium (containing 100 mg/L of ampicillin) at 37° C. Eighteen hours after starting the cultivation, the resulting culture medium was inoculated to 100 mL of new LB medium (containing 100 mg/L of ampicillin), and cultured with shaking using a 500 mL flask at 37° C. for 24 hours. The resulting microbial cells were collected by centrifugation (6,000 rpm, 5 minutes), and suspended in 5 mL of 50 mM Tris-HCl buffer (pH 8.0). The microbial solution was sonicated to disrupt the microbial cells. The resulting solution was centrifuged at 6,000 rpm for 15 minutes and a supernatant fraction was collected. The collected solution was heated at 60° C. for 20 minutes and then rapidly cooled on ice. The cooled solution was centrifuged at 6,000 rpm for 15 minutes and a supernatant (about 5 mL) was collected again. This solution was sterilized using the disc filter (Millex GP. 0.22 Millipore, USA). And, the solution was ultrafiltrated and concentrated using Amicon-Ultra-15 (NMWL. 50000, Millipore, USA), and the buffer in which the protein was dissolved was replaced with Tris-HCl buffer (50 mM Tris-HCl pH 8.0) to obtain 2.5 mL of a protein solution.

To purify CcDT from the resulting protein solution, anion exchange chromatography was used. Specifically, 2.5 mL of the protein solution was applied to HiLoard 26/10 Q-Sepharose High Performance column (GE healthcare, USA) equilibrated with 50 mM Tris-HCl buffer (pH 8.0). The separation/purification was carried out at a flow rate of 4.0 mL/minute by making a concentration gradient of the salt from 0 mM to 500 mM NaCl in 50 mM Tris-HCl buffer (pH 8.0), and fractions containing CcDT were collected.

Example 9

Confirmation of Formation of CcDT Multimer

The obtained CcDT was stained with 3% PTA (phosphotungstic acid), and analyzed under the transmission electron microscope. As a result, it was found that CcDT formed a cage-like multimer having a diameter of about 9 nm, as is similar to CDT.

Example 10

Confirmation of Binding Between Fusion Protein CcDT and Carbon Nanotube

The binding between CcDT and CNT was measured by QCM method. First, the surface of the gold sensor was washed by placing 50 µL of a washing solution [in which 98% (w/v) sulfuric acid and 30% (w/v) hydrogen peroxide water were mixed at 3:1] on the gold sensor for the measurement for five minutes and then washing it out with water. CNT was mixed at a final concentration of 1 mg/mL with 1% SDS solution, and the mixture was sonicated for 30 minutes to prepare a CNT solution. 2 µL of this CNT solution was mounted on the gold electrode and dried naturally at room temperature. After the drying, the sensor was washed twice with water to wash out CNT not bound to the sensor. The sensor was further washed once with phosphate buffer A (50 mM potassium phosphate buffer containing 0.001% (w/v) Tween 20, pH 7.0). This CNT sensor was attached to the main body (Affinix QNµ, Initium), and the frequency value was stabilized by dropping the phosphate buffer A on the CNT sensor and leaving it stand at room temperature for 30 minutes to one hour. After stabilizing the frequency value, 500 µL of a reaction solution containing CcDT at a final concentration of 1 mg/L was added, and the change of the frequency was measured.

As a result, it was observed that CcDT having CNHBP could bind to CNT more abundantly than DT having no CNHBP. Therefore, it was found that CcDT has the stronger ability to bind to CNT than DT. It was speculated that this ability of CcDT to bind to CNT depended on CNHBP.

Example 11

Confirmation of Binding Between Fusion Protein CcDT and Titanium Oxide

The binding between CcDT and titanium oxide was measured by QCM method. First, the surface of the titanium oxide sensor was washed by placing 50 µL of the washing solution [in which 98% (w/v) sulfuric acid and 30% (w/v) hydrogen peroxide water were mixed at 3:1] on the sensor for the measurement for five minutes and then washing it out with water. The titanium oxide sensor was attached to the main body (Affinix QNµ, Initium), and the frequency value was stabilized by dropping the phosphate buffer B (50 mM potassium phosphate buffer, pH 7.0) on the titanium oxide sensor and leaving it stand at room temperature for 30 minutes to one hour. After stabilizing the frequency value, 500 µL of a reaction solution containing CcDT was added at a final concentration of 1 mg/L, and the change of the frequency was measured.

As a result, it was observed that CcDT having TBP was bound to titanium oxide more abundantly than CD having no TBP. Therefore, it was found that CcDT had the stronger ability to bind to titanium oxide than CD. It was speculated that this ability of CcDT to bind to titanium oxide depended on TBP.

Example 12

Binding between Metal Particle-encapsulating Fusion Protein CDT and CNT

First, an iron oxide nanoparticle was formed in an internal cavity of a CDT multimer. Specifically, 1 mL of HEPES buffer containing CDT (80 mM HEPES/NaOH, pH 7.5 containing 0.5 mg/mL of CDT and 1 mM ammonium iron sulfate each at a final concentration) was prepared, and left stand at 4° C. for 3 hours. Then, this buffer was centrifuged (15,000 rpm, 5 minutes), and a supernatant containing the protein was collected. This supernatant was ultrafiltrated and concentrated using Amicon-Ultra-15 (NMWL. 50000, Millipore, USA) and the buffer in the solution of the CDT multimer having the iron oxide nanoparticle in its internal cavity (Fe-CDT) was replaced with water to obtain a protein solution. A potassium phosphate buffer (50 mM potassium phosphate (pH 6.0) containing 0.3 mg/mL Fe-CDT and 0.3 mg/mL CNT each at a final concentration) containing CNT and the CDT multimer having the iron oxide nanoparticle in its internal cavity was prepared using this protein solution. An ultrasonic pulse treatment (200 W, duty 10%) for one second was given to the prepared solution every 3 seconds for total 5 minutes on ice using Digital Sonifier 450 (Branson, USA). The Fe-CDT-CNT mixed solution treated by the ultrasonic pulse was centrifuged (15,000 rpm, 5 minutes) to obtain a CNT/Fe-CDT complex in which many CDT multimers were bound to CNT. The result is shown from a transmission electron microscopic image of the complex of CNT and CNHBP-Dps-TBP (CDT multimer) having the iron oxide nanoparticle in its internal cavity. The transmission electron microscopic image was obtained by photographing the sample stained with 3% TPA.

As a result, it could be confirmed that the complex (CNT/Fe-CDT complex) of CNT and CNHBP-Dps-TBP (CDT multimer) having the iron oxide nanoparticle in its internal cavity had been obtained.

Example 13

Preparation Example of CNT/Fe-CDT/Ti Complex

The titanium precursor, titanium (IV) bis(ammonium lactato)dihydroxide (Sigma, 388165) was added to the obtained CNT/Fe-CDT complex solution such that the final concentration of the precursor became 2.5% by weight, and the mixture was left stand at room temperature (24° C.)

Samples were centrifuged (15,000 rpm, 5 minutes) 30 minutes and 15 hours after starting the reaction, and pellets were collected. The pellet was washed three times with water, and finally suspended in water to obtain an aqueous solution of CNT/Fe-CDT/Ti.

A transmission electron microscopic image of a black precipitate obtained by adding the titanium precursor to the complex of CNT and CNHBP-Dps-TBP (CDT multimer) shows the iron oxide nanoparticle in its internal cavity. When the aqueous solution of CNT/Fe-CDT/Ti not stained was analyzed under TEM, the CDT multimers encapsulating the iron oxide nanoparticles in their internal cavities could be observed in a black rod-shaped structure.

This black rod-shaped structure could be speculated to contain titanium from the result of EDS analysis. A surface area of the titanium nano-rod structure, which appeared to be increased by the CDT multimers, was analyzed from this TEM image. As a result, it could be speculated from the TEM image that 64 CDT multimers were encapsulated in the titanium nano-rod structure having a length of 102 nm in a lengthwise direction, and a diameter of 31 nm in a direction orthogonal to the lengthwise direction. The surface area of the titanium nano-rod structure is $1.1 \times 10^4$ nm$^2$. The surface area of the CDT multimer having a diameter of 9 nm is 254 nm$^2$. A sum of the surface areas of 64 CDT multimers is $1.6 \times 10^4$ nm$^2$. That is, the surface area per 100 nm of the length in the lengthwise direction of the titanium nano-rod structure encapsulating the CDT multimers observed in this case is $2.6 \times 10^4$ nm$^2$, and could be estimated to be 2.4 times larger than $1.1 \times 10^4$ nm$^2$ that was the surface area per 100 nm of the length in the lengthwise direction of the titanium nano-rod structure which did not encapsulate the CDT multimer.

Since the iron oxide nanoparticle encapsulated in the CDT multimer could be introduced into the titanium film, it is expected to introduce the metal nanoparticle of nickel, cobalt, manganese, phosphorus, uranium, beryllium, aluminium, cadmium sulfide, cadmium selenide, palladium, chromium, copper, silver, gadolium complex, platinum cobalt, silicon oxide, cobalt oxide, indium oxide, platinum, gold, gold sulfide, zinc selenide, and cadmium selenium, which are predicted to be able to encapsulated in the CDT multimer, into a titanium film and a titanium oxide film which coat CNT.

Subsequently, 10 µL of an aqueous solution of CNT/Fe-CDT/Ti was placed on a silicon substrate treated with UV/ozone (115° C., 5 minutes, 1 mL/minute) and coated with an SiO$_2$ film having a thickness of 10 nm, and treated with heat at 450° C. for 30 minutes. Subsequently the complex was left stand at and cooled to room temperature, and analyzed under a scanning electron microscope (SEM). A scanning electron microscopic image of a structure obtained by heating shows the complex of CNT and CNHBP-Dps-TBP (CDT multimer) coated with titanium oxide.

As a result, an appearance where a circumference of CNT observed as a fibrous shape was covered with particulate structures and film-shaped structures was observed. Also, from the analysis by EDS (energy dispersive x-ray spectrometry), it was suggested that the structures that coated CNT was composed of the titanium oxide.

Example 14

Preparation Example of CNT/TiO$_2$ Complex

First, CDT at a final concentration of 0.3 mg/mL and CNT (carbon nanotube single walled, Sigma, 519308) at a final concentration of 0.3 mg/mL were added to 50 mM potassium phosphate buffer (pH 6.0). Subsequently, 40 mL of the obtained solution was sonicated (200 W, 25%) on ice using Digital Sonifier (Branson, USA) in cycles of sonicating the solution for one second and resting the sonication for three seconds, and the sonication treatment was continued for 5 minutes. A thick element having a diameter of 10 mm was used for the sonication. After the sonication, the solution was transferred to a 50 mL tube, and CNT that had not been bound to the CDT multimer was removed by centrifugation at 8,500 rpm for 10 minutes. Titanium (IV) bis(ammonium lactato) dihydroxide (Sigma, 388165) was added at a final concentration of 2.5% by weight to this solution, and the mixture was left stand at room temperature for 2 hours. In consequence, precipitation of an aggregate was observed. Subsequently, the solution in a 50 mL centrifuge tube was centrifuged at 8,500 rpm for 10 minutes and the precipitate was collected to purify a CNT/CDT/Ti complex. The complex was further washed by adding 40 mL of water and centrifuging it. Finally, 0.8 mL of water was added and the solution was transferred to a 1.5 mL of microtube. Subsequently, 200 µL of the obtained CNT/CDT/Ti solution was placed on a quartz board and heated at temperature ranging from 450° C. to 800° C. (at each temperature of 500° C., 600° C., 700° C. and 800° C.) for 30 minutes (temperature rising rate: 50° C./minute).

Black powder obtained by the burning at each temperature was stained with 3% PTA, and analyzed under TEM. Transmission electron microscopic images of the structures obtained by heating show the complex of CNT and CNHBP-Dps-TBP (CDT multimer) coated with titanium oxide.

When the complex was burned at 500° C., many linear structures could be observed. When the complex was burned at 600° C., the linear structure could be scarcely observed. When the complex was burned at 700° C. or above, the linear structure could not be observed at all.

In order to further examine a crystalline condition of the obtained black powder, the black powder obtained by burning at 450° C. was analyzed by X ray diffraction (XRD). The result of the XRD analysis of the structure obtained by burning showed the complex of CNT and CNHBP-Dps-TBP (CDT multimer) coated with titanium oxide at 450° C.

Peaks specific to (101) and (200) phases of anatase type TiO$_2$ crystal could be observed.

However, it was estimated that TiO was also included because peaks other than those of the anatase type $TiO_2$ crystal were also observed. Likewise, the black powders obtained by burning at 500° C. and 600° C. were analyzed by the XRD analysis, and the similar peak patterns were observed. Thus, it was suggested that the black powder obtained by burning at least at 600° C. or below included an anatase type $TiO_2$ crystal having a photocatalytic activity.

Example 15

Production Example of Photoelectric Conversion Element (Dye-sensitized Solar Cell)

The CNT/CDT/Ti complex obtained in Example 14 was used as a material for a photoelectric conversion layer of an photoelectric conversion element (dye-sensitized solar cell) to evaluate its effect on properties of the dye-sensitized solar cell. The production of the dye-sensitized solar cell was carried out by modifying the protocols by Solaronix.

First, a CNT(SWNT)/CDT/Ti corresponding to 1 mL of a reaction solution was synthesized by the above method, washed with water and suspended in an ethanol solution. The CNT(SWNT)/CDT/Ti complex was blended into a titanium oxide paste (Ti-Nanoxide D, Solaronix), and used as a material of a dye-sensitized solar cell. In order to form a photoelectric conversion layer, pieces of mending tape (3M Company, a thickness of about 100 μm) cut into 5 mm and doubly attached were attached to both ends of an FTO substrate (fluorine-doped tin oxide, Solaronix), respectively that was a transparent electrode substrate cut into 25 mm×25 mm. An interval between the tape pieces was 10 mm.

The titanium oxide paste containing the CNT(SWNT)/CDT/Ti complex was placed between the tape pieces, extended flatly using a slide glass, and left stand at 30° C. for 30 minutes to dry the titanium oxide paste. The substrate on which the titanium oxide paste had been placed was placed in a burning furnace and burned at 450° C. for 30 minutes. The temperature was raised at 90° C./minute. After the burning, the substrate was naturally cooled to 100° C. or below. 1 mL of 0.2 g/L ruthenium (Ru) dye-sensitizing solution (N719, dissolved in dry ethanol, Solaronix) was applied to the burned substrate, which was then left stand at room temperature for 24 hours. The electrode substrate stained red by being left stand for 24 hours was washed with ethanol to remove the dye not adsorbed to the titanium oxide surface, dried using a dryer, and used as a photoelectrode.

A dye-sensitized solar cell was made using a Pt electrode (opposite electrode) obtained by coating the surface of the fluorine-doped tin oxide (FTO) film with platinum (Pt) having a thickness of 50 nm, and the structure comprising the above photoelectrode.

A sealing sheet (SX1170-25, Solaronix) was used as a sealing material, and heating at 120° C. for 5 minutes was given using a hotplate. Araldite Rapid (Showa Highpolymer Co., Ltd.) that was an epoxy-based adhesive was applied to an adhered surface not completely sealed and left stand at 30° C. for 2 hours to seal completely. Finally, an iodine electrolyte solution (Solaronix) was added to obtain the dye-sensitized solar cell.

The produced dye-sensitized solar cell was evaluated by illuminating with light at an intensity of 100 mw/cm² with a xenon lamp.

An open voltage Voc (V), a short-circuit current density Jsc (mA/cm²), a fill factor FF, and a photoelectric conversion efficiency η (%) were evaluated as properties of the dye-sensitized solar cell. In the solar cell, a rate of one converted into electric power in incident energy by the illuminated light is referred to as the photoelectric conversion efficiency η. A current density measured when the voltage is 0 V is referred to as the short-circuit current density Jsc, and the voltage when a current does not flow is referred to as the open voltage Voc. A relation of photoelectric conversion efficiency η=Jsc×Voc×FF is established, and FF is referred to as the fill factor. The results are shown in Table 8.

As is evident from Table 8, the short-circuit current density was 12 mA/cm² in the dye-sensitized solar cell [device 2 (−)] comprising a photoelectrode formed of the titanium oxide paste alone. On the other hand, the short-circuit current density was 15 mA/cm² in the dye-sensitized solar cell [device 1 (+)] using the titanium oxide paste in which the CNT (SWNT)/CDT/Ti complex had been blended as the functional material of the photoelectrode. Thus, an amount of the current was increased by 25% by using the CNT (SWNT)/CDT/Ti complex as the functional material of the electrode. Further, the photoelectric conversion efficiency was increased to 1.4 times by using the titanium oxide paste in which the CNT (SWNT)/CDT/Ti complex had been blended as the functional material of the photoelectrode.

TABLE 8

|  | CNT/CDT/Ti | Voc (V) | Jsc (mA/cm²) | FF | η (%) |
| --- | --- | --- | --- | --- | --- |
| Device 1 | + | 0.67 | 15.3 | 0.39 | 4.0 |
| Device 2 | − | 0.64 | 12.3 | 0.36 | 2.8 |

Example 16

Production Example of Photoelectric Conversion Element (Dye-Sensitized Solar Cell)

The CNT/CDT/Ti complex obtained in Example 14 was used as the material for the photoelectric conversion layer of the photoelectric conversion element (dye-sensitized solar cell), and effects of the complex on the properties of the dye-sensitized solar cell was evaluated. The production of the dye-sensitized solar cell was carried out by modifying the protocol by Solaronix.

First, the CNT(SWNT)/CDT/Ti corresponding to 1 mL of a reaction solution was synthesized by the above method, washed with water and suspended in an ethanol solution. The CNT(SWNT)/CDT/Ti complex was blended into the titanium oxide paste (Ti-Nanoxide D, Solaronix) so that the complex was contained at a final concentration of 0.2% by weight in a titanium oxide electrode after the burning, and used as the material of the dye-sensitized solar cell. In order to form the photoelectric conversion layer, the FTO substrate (fluorine-doped tin oxide, Solaronix) that was the transparent electrode substrate cut into 25 cm×25 cm was immersed in an aqueous solution of 40 mM titanium tetrachloride at 80° C. for 30 minutes. Tape pieces of the mending tape (3M Company, thickness: about 100 μm) cut into 5 mm and doubly attached were attached to the both ends of the FTO substrate. The interval between the tape pieces was 5 mm.

The titanium oxide paste containing the CNT(SWNT)/CDT/Ti complex was placed between the tape pieces, extended flatly using the slide glass, and left stand at 30° C. for 30 minutes to dry the titanium oxide paste. The substrate on which the titanium oxide paste had been placed was placed in the burning furnace and burned at 450° C. for 30 minutes. The temperature was raised at 90° C./minute. After the burning, the substrate was naturally cooled to 100° C. or below. After the burning, a titanium oxide portion on the FTO substrate was cut into a 5 mm×10 mm square, this substrate was immersed in 1 mL of 0.2 g/L ruthenium (Ru) dye-sensitizing solution (N719, dissolved in dry ethanol, Solaronix), and left stand at room temperature for 24 hours. The electrode substrate stained red by being left stand for 24 hours was washed with ethanol to remove the dye not adsorbed to the titanium oxide surface, dried at room temperature, and used as a photoelectrode (device 11).

For controls, a device using a photoelectrode made from a titanium oxide electrode containing 0.2% by weight of a CNT/titanium oxide complex synthesized by oxidation treatment (device 12), a device using a photoelectrode made from a titanium oxide electrode containing 0.2% by weight of CNT (device 13), and a device using a photoelectrode made from a titanium oxide electrode containing no CNT (device 14) were made. The CNT/titanium oxide complex was synthesized by the oxidation treatment with reference to the method in the reference (W. Wang et al. (2005) Journal of Molecular Catalysis A: Chemical, 235, 194-199). Specifically, 34 mL of a titanium butoxide solution (0.1 mol) was added to 200 mL of ethanol, and the mixture was stirred at room temperature for 30 minutes. Subsequently, 28 mL of nitric acid (35% by weight) was added, then an appropriate amount of CNT was added, and the mixture was stirred at room temperature overnight until the mixture became gelatinous. Subsequently, a precipitate was collected by centrifugation and dried by leaving it stand at 80° C. overnight to obtain the CNT/titanium oxide complex.

A dye-sensitized solar cell was made using a Pt electrode (opposite electrode) obtained by coating the surface of the fluorine-doped tin oxide (FTO) film with platinum (Pt) having a thickness of 50 nm, and the structure comprising the above photoelectrode.

A sealing sheet (SX1170-25, Solaronix) was used as a sealing material, and the heating at 120° C. for 5 minutes was given using the hotplate. Araldite Rapid (Showa Highpolymer Co., Ltd.) that was the epoxy-based adhesive was applied to the adhered surface not completely sealed and left stand at 30° C. for 2 hours to seal completely. Finally, the iodine electrolyte solution (Solaronix) was added to obtain the dye-sensitized solar cell.

The produced dye-sensitized solar cell was evaluated by illuminating with light at an intensity of 100 mW/cm$^2$ with the xenon lamp.

The open voltage Voc (V), the short-circuit current density Jsc (mA/cm$^2$), the fill factor FF, and the photoelectric conversion efficiency η(%) were evaluated as the properties of the dye-sensitized solar cell. The results are shown in Table 9.

As is evident from Table 9, the larger short-circuit current density was measured in the dye-sensitized solar cells comprising the photoelectrode formed from the titanium oxide paste containing a nanomaterial (devices 11, 12, and 13) than in the dye-sensitized solar cell comprising the photoelectrode formed from the titanium oxide paste alone (device 14). In particular, the short-circuit current density was increased by 180% by using the CNT(SWNT)/CDT/Ti complex as the functional material of the electrode. The short-circuit current density in the device using the complex of titanium oxide and CNT synthesized using CDT (device 11) as the functional material of the electrode was larger than the short-circuit current density in the device using CNT alone as the functional material of the electrode (device 13) and the short-circuit current density in the device using the complex of titanium oxide and CNT synthesized by the oxidation treatment as the functional material of the electrode (device 12).

First, for a reason why the short-circuit current density was enhanced by introducing CNT into the titanium oxide electrode, this was thought to be because generated carrier passed through CNT and could move to a conductive film prior to being bound again to decrease the amount of the current. It was also thought that by forming the complex of CNT and titanium oxide by the CDT treatment or the oxidation treatment, CNT and titanium oxide could be adhered tightly and resistance between CNT and titanium oxide was reduced. Thus, it was thought that the carrier generated in the circumference of titanium oxide more efficiently moved to CNT than in the case of introducing untreated CNT into the titanium oxide paste. In the complex of titanium oxide/CNT synthesized by an acid treatment, it has been thought that the structure of CNT is partially broken by the acid and the movement of the carrier in CNT is inhibited. However, if the protein CDT is used, the CNT/titanium oxide complex can be synthesized without impairing the structure of CNT. Further, it was thought that the surface area was enhanced by the empty holes derived from CDT and the dye could be supported more abundantly. Thus, it was thought that the generated carrier was more abundant, a moving rate of the carrier in CNT was kept more stably, and thus the larger short-circuit current was observed in the complex of titanium oxide/CNT synthesized using CDT than in the complex of titanium oxide/CNT synthesized by the acid treatment.

As a result of the enhanced short-circuit current density, the photoelectric conversion efficiency η in the device using the titanium oxide paste in which CNT(SWNT)/CDT/Ti had been blended (device 11) as the functional material of the photoelectrode was 2.2 times larger than the photoelectric conversion efficiency η in the device using the titanium oxide paste not containing CNT (device 14) as the functional material of the photoelectrode. The highest photoelectric conversion efficiency was measured in the device using the titanium oxide paste in which CNT(SWNT)/CDT/Ti had been blended as the functional material of the photoelectrode among the devices produced this time. Therefore, it was found that the performance of the solar cell could be enhanced by using the complex of titanium oxide and CNT synthesized using CDT under the mild condition.

It was also confirmed that the higher short-circuit current density and the higher photoelectric conversion efficiency η than in the devices produced in Example 15 could be obtained by treating the FTO substrate with titanium tetrachloride or blending the CNT(SWNT)/CDT/Ti complex at a final concentration of 0.2% by weight into the titanium oxide electrode.

TABLE 9

|  | Voc (V) | Jsc (mA/cm$^2$) | FF | η (%) |
| --- | --- | --- | --- | --- |
| Device 11 | 0.73 | 13.1 | 0.68 | 6.5 |
| Device 12 | 0.76 | 8.9 | 0.73 | 5.0 |
| Device 13 | 0.75 | 8.2 | 0.72 | 4.5 |
| Device 14 | 0.71 | 7.3 | 0.58 | 3.0 |

Example 17

Production of Strain for Expressing Fusion Protein CNHBP-Dps-ZnO1' (CDZ)

The metal-encapsulating protein Dps from *Listeria innocua*, the N-terminus of which is fused with the carbon nanohorn-binding peptide (abbreviated as CNHBP and consisting of the amino acid sequence DYFSSPYYEQLF (SEQ ID NO:6), see International Publication No. WO2006/068250), the C-terminus of which is fused with a zinc oxide-precipitating peptide (abbreviated as ZnO1' and consisting of the amino acid sequence EAHVMH-KVAPRPGGGSC (SEQ ID NO:30), see Umetsu et al., Adv. Mater., 17, 2571-2575 (2005)) was constructed (abbreviated as CNHBP-Dps-ZnO1' or CDZ, SEQ ID NOS:31 and 32) by the following procedure.

First, PCR was carried out using pET20-CDT as the template DNA, and the oligonucleotides consisting of the nucleotide sequence represented by SEQ ID NO:11 and the nucleotide sequence of tttGGATCCttaAcaACTAccTccAc-cAggAcGTggAgcAacTttAtgcatTacAtgTg cTtcttctaatg-gagctttc (SEQ ID NO:33) as the primers. The obtained PCR product was purified using Wizard SV Gel and PCR Clean-Up System (Promega, USA) and digested with the restriction enzymes DpnI and BamHI. The PCR product digested with the restriction enzymes was self-ligated using the T4 ligase (Promega, UAS). E. coli BL21 (DE3) (Nippon Gene, Japan) was transformed with the self-ligated PCR product to construct BL21 (DE3) possessing the expression plasmid carrying the gene encoding Dps (CDZ), the N-terminus and the C-terminus of which were fused to the carbon nanohorn-binding peptide and the zinc oxide-precipitating peptide, respectively (pET20-CDZ).

Example 18

Purification of Fusion Protein CDZ

BL20 (DE3)/pET20-CDZ was inoculated to 100 mL of the LB medium (containing 100 mg/L of ampicillin), and cultured with shaking using a 500 mL flask at 37° C. for 24 hours. The resulting microbial cells were collected by centrifugation (6,000 rpm, 5 minutes) and suspended in 5 mL of 50 mM Tris-HCl buffer (pH 8.0). The microbial solution was sonicated to disrupt the microbial cells. The resulting solution was centrifuged at 6,000 rpm for 15 minutes to collect a supernatant fraction. The collected solution was heated at 60° C. for 20 minutes and then cooled on ice rapidly after the heating. The cooled solution was centrifuged at 6,000 rpm for 15 minutes to collect a supernatant (about 5 mL) again. This solution was sterilized using the disc filter (Millex GP 0.22 μm, Millipore, USA). This solution was ultrafiltrated and concentrated using Amicon-Ultra-15 (NMWL. 50000, Millipore, USA), and the buffer in which the protein was dissolved was replaced with Tris-HCl buffer (50 mM Tris-HCl solution, pH 8.0) to obtain 2.5 mL of a protein solution.

Anion exchange chromatography was used for purifying CDZ from the resulting protein solution. Specifically, 2.5 mL of the protein solution was applied to HiLoard 26/10 Q-Sepharose High Performance column (GE healthcare, USA) equilibrated with 50 mM Tris-HCl buffer (pH 8.0). The separation/purification was carried out at a flow rate of 4.0 mL/minute by making the concentration gradient of the salt from 0 mM to 500 mM NaCl in 50 mM Tris-HCl buffer (pH 8.0), and fractions containing CDZ were collected. Further, the collected solution was ultrafiltrated and concentrated using Amicon-Ultra-15 (NMWL. 50000, Millipore, USA), and the buffer in which the protein was dissolved was replaced with pure water to obtain a CDZ solution.

Example 19

Confirmation of Formation of CDZ Multimer

CDZ dissolved in 50 mM Tris-HCl buffer (pH 8.0) before the buffer was replaced with pure water was stained with 3% PTA (phosphotungstic acid), and analyzed under the transmission electron microscope. As a result, it was found that CDZ formed the cage-like multimer having a diameter of about 9 nm, as is similar to CDT.

Example 20

Facilitation of White Precipitate Formation from Aqueous Solution of Zinc Sulfate by CDZ First, CDZ, CDT, or CD dissolved in pure water was added at a final concentration of 0.1 mg/mL to an aqueous solution of 0.1 M zinc sulfate. After the solution was left stand at room temperature for one hour, a turbidity of the solution was measured using the light at 600 nm. A white precipitate occurred prominently in the solution containing CDZ. It was thought that this white precipitate was zinc hydroxide or zinc oxide. On the other hand, no precipitate occurred at all in the solution containing no protein. It is known that zinc hydroxide becomes zinc oxide by being heated at about 125° C. From above, it was suggested that CDZ had an activity to precipitate the zinc compound.

Example 21

Confirmation of Binding Ability of CNHBP in CDZ

An activity of the carbon nanohorn-binding peptide (CN-HBP) fused to the N-terminus of CDZ was examined. CDZ and CNT (Sigma, 519308, carbon nanotube single walled) were added at a final concentration of 0.3 mg/mL to potassium phosphate buffer (50 mM, pH 6.0). The ultrasonic pulse (200 W, duty 206) for one second with an interval of 3 seconds was given to this solution for 5 minutes using Digital Sonifier 450 (Branson, USA). The sonicated CDZ/CNT mixed solution was centrifuged (15,000 rpm, 5 minutes), a protein/CNT complex included in a supernatant was stained with 3% PTA and observed under the transmission electron microscope (JEM-2200FS, 200 kV).

As a result, an appearance where CDZ was bound to the circumference of CNT could be observed in the solution containing CDZ having CNHBP at its N-terminus. Therefore, it was found that CDZ retained an activity of binding to CNT.

This application claims benefit to International Application No. PCT/JP2011/079529, filed Dec. 20, 2011, and Japanese patent application Nos. 2010-286470 and 2011-173230, all of which are incorporated herein by reference.

The invention claimed is:

1. A fusion protein, comprising:
   a DPS,
   a first peptide portion capable of binding to a first target substance, and
   a second peptide portion capable of binding to a second target substance,
   wherein
   the DPS is a protein consisting of an amino acid sequence having 95% or more identity to an amino acid sequence represented by SEQ ID NO: 4 or SEQ ID NO: 29,
   the first peptide portion and the second peptide portion are each capable of binding to a different target substance, and
   the first peptide portion and the second peptide portion are each independently capable of binding to a metal material, a silicon material or a carbon material.

2. The fusion protein according to claim 1, wherein a C-terminal part of the first peptide portion is fused to an N-terminal part of the Dps and an N-terminal part of the second peptide portion is fused to a C-terminal part of the Dps.

3. The fusion protein according to claim 1, wherein the metal material is a titanium material or a zinc material.

4. The fusion protein according to claim 1, wherein the silicon material is silicon or an oxide of silicon.

5. The fusion protein according to claim 1, wherein the carbon material is a carbon nanomaterial.

6. The fusion protein according to claim 1, wherein the fusion protein is a protein consisting of an amino acid sequence having 95% or more amino acid sequence identity to an amino acid sequence represented by SEQ ID NO:2, SEQ ID NO:27, or SEQ ID NO:32.

7. The fusion protein according to claim 1, wherein the peptide portion capable of binding to the metal material has an action for mineralization.

8. The fusion protein according to claim 1, which comprises the amino acid sequence of SEQ ID NO: 2, 27 or 23.

9. The fusion protein according to claim 1, which has the amino acid sequence of SEQ ID NO: 2, 27 or 23.

10. The fusion protein according to claim 1, wherein one of the a first peptide portion or the second peptide portion is capable of binding to the carbon material and the other peptide portion is capable of binding to the metal material or the silicon material.

11. A multimer of a fusion protein, comprising:
    a DPS,
    a first peptide portion capable of binding to a first target substance, and
    a second peptide portion capable of binding to a second target substance,
    wherein
    the DPS is a protein consisting of an amino acid sequence having 95% or more identity to an amino acid sequence represented by SEQ ID NO: 4 or SEQ ID NO: 29,
    the first peptide portion and the second peptide portion are each capable of binding to a different target substance,
    the first peptide portion and the second peptide portion are each capable of binding to a metal material, a silicon material or a carbon material, and
    the multimer has an internal cavity.

12. The multimer according to claim 11, wherein the multimer contains a substance in the internal cavity.

13. A complex comprising the multimer according to claim 11 or 12, and a first and second substances, wherein the first target substance is bound to the first peptide portion in the fusion protein and the second target substance is bound to the second peptide portion in the fusion protein.

* * * * *

SEQUENCE LISTING

<160> NUMBER OF SEQ ID NOS: 33

<210> SEQ ID NO 1
<211> LENGTH: 531
<212> TYPE: DNA
<213> ORGANISM: Artificial Sequence
<220> FEATURE:
<223> OTHER INFORMATION: Nucleotide sequence encoding an amino acid sequence of fusion protein
<220> FEATURE:
<221> NAME/KEY: CDS
<222> LOCATION: (1)..(531)

<400> SEQUENCE: 1

```
atg gac tac ttc tct tct ccg tac tac gaa cag ctg ttt atg aaa aca      48
Met Asp Tyr Phe Ser Ser Pro Tyr Tyr Glu Gln Leu Phe Met Lys Thr
1               5                   10                  15 atc aac tca gta gac aca aag gaa ttt ttg aat cat caa gta gcg aat      96
Ile Asn Ser Val Asp Thr Lys Glu Phe Leu Asn His Gln Val Ala Asn
                20                  25                  30 tta aac gta ttc aca gta aaa att cat caa att cat tgg tat atg aga     144
Leu Asn Val Phe Thr Val Lys Ile His Gln Ile His Trp Tyr Met Arg
            35                  40                  45 ggc cac aac ttc ttc act tta cat gaa aaa atg gat gat tta tat agc     192
Gly His Asn Phe Phe Thr Leu His Glu Lys Met Asp Asp Leu Tyr Ser
        50                  55                  60 gaa ttc ggt gaa caa atg gat gaa gta gca gaa cgt tta ctt gcc att     240
Glu Phe Gly Glu Gln Met Asp Glu Val Ala Glu Arg Leu Leu Ala Ile
65                  70                  75                  80 ggt gga agc cca ttc tcg act tta aaa gag ttt tta gaa aat gcg agt     288
Gly Gly Ser Pro Phe Ser Thr Leu Lys Glu Phe Leu Glu Asn Ala Ser
                85                  90                  95 gta gaa gaa gct cct tat aca aaa cct aaa act atg gat caa tta atg     336
Val Glu Glu Ala Pro Tyr Thr Lys Pro Lys Thr Met Asp Gln Leu Met
                100                 105                 110 gaa gac tta gtt ggt aca tta gaa tta ctt aga gac gaa tat aaa caa     384
Glu Asp Leu Val Gly Thr Leu Glu Leu Leu Arg Asp Glu Tyr Lys Gln
            115                 120                 125 ggc att gag cta act gac aaa gaa ggc gac gat gta aca aac gat atg     432
Gly Ile Glu Leu Thr Asp Lys Glu Gly Asp Asp Val Thr Asn Asp Met
        130                 135                 140 cta att gca ttt aaa gct agc att gac aaa cat atc tgg atg ttc aaa     480
Leu Ile Ala Phe Lys Ala Ser Ile Asp Lys His Ile Trp Met Phe Lys
145                 150                 155                 160 gca ttc ctt gga aaa gct cca tta gaa atg cgc aaa ctt ccg gat gcg     528
Ala Phe Leu Gly Lys Ala Pro Leu Glu Met Arg Lys Leu Pro Asp Ala
                165                 170                 175 taa                                                                 531
```

<210> SEQ ID NO 2
<211> LENGTH: 176
<212> TYPE: PRT
<213> ORGANISM: Artificial Sequence
<220> FEATURE:
<223> OTHER INFORMATION: Synthetic Construct

<400> SEQUENCE: 2

```
Met Asp Tyr Phe Ser Ser Pro Tyr Tyr Glu Gln Leu Phe Met Lys Thr
1               5                   10                  15

Ile Asn Ser Val Asp Thr Lys Glu Phe Leu Asn His Gln Val Ala Asn
                20                  25                  30

Leu Asn Val Phe Thr Val Lys Ile His Gln Ile His Trp Tyr Met Arg
            35                  40                  45

Gly His Asn Phe Phe Thr Leu His Glu Lys Met Asp Asp Leu Tyr Ser
        50                  55                  60

Glu Phe Gly Glu Gln Met Asp Glu Val Ala Glu Arg Leu Leu Ala Ile
65                  70                  75                  80
```

```
Gly Gly Ser Pro Phe Ser Thr Leu Lys Glu Phe Leu Glu Asn Ala Ser
            85                  90                  95

Val Glu Glu Ala Pro Tyr Thr Lys Pro Lys Thr Met Asp Gln Leu Met
            100                 105                 110

Glu Asp Leu Val Gly Thr Leu Glu Leu Leu Arg Asp Glu Tyr Lys Gln
            115                 120                 125

Gly Ile Glu Leu Thr Asp Lys Glu Gly Asp Asp Val Thr Asn Asp Met
            130                 135                 140

Leu Ile Ala Phe Lys Ala Ser Ile Asp Lys His Ile Trp Met Phe Lys
145                 150                 155                 160

Ala Phe Leu Gly Lys Ala Pro Leu Glu Met Arg Lys Leu Pro Asp Ala
                165                 170                 175

<210> SEQ ID NO 3
<211> LENGTH: 471
<212> TYPE: DNA
<213> ORGANISM: Listeria innocua
<220> FEATURE:
<221> NAME/KEY: CDS
<222> LOCATION: (1)..(471)

<400> SEQUENCE: 3 atg aaa aca atc aac tca gta gac aca aag gaa ttt ttg aat cat caa       48
Met Lys Thr Ile Asn Ser Val Asp Thr Lys Glu Phe Leu Asn His Gln
1               5                   10                  15 gta gcg aat tta aac gta ttc aca gta aaa att cat caa att cat tgg      96
Val Ala Asn Leu Asn Val Phe Thr Val Lys Ile His Gln Ile His Trp
                20                  25                  30 tat atg aga ggc cac aac ttc ttc act tta cat gaa aaa atg gat gat     144
Tyr Met Arg Gly His Asn Phe Phe Thr Leu His Glu Lys Met Asp Asp
            35                  40                  45 tta tat agc gaa ttc ggt gaa caa atg gat gaa gta gca gaa cgt tta     192
Leu Tyr Ser Glu Phe Gly Glu Gln Met Asp Glu Val Ala Glu Arg Leu
        50                  55                  60 ctt gcc att ggt gga agc cca ttc tcg act tta aaa gag ttt tta gaa     240
Leu Ala Ile Gly Gly Ser Pro Phe Ser Thr Leu Lys Glu Phe Leu Glu
65                  70                  75                  80 aat gcg agt gta gaa gaa gct cct tat aca aaa cct aaa act atg gat     288
Asn Ala Ser Val Glu Glu Ala Pro Tyr Thr Lys Pro Lys Thr Met Asp
                85                  90                  95 caa tta atg gaa gac tta gtt ggt aca tta gaa tta ctt aga gac gaa     336
Gln Leu Met Glu Asp Leu Val Gly Thr Leu Glu Leu Leu Arg Asp Glu
            100                 105                 110 tat aaa caa ggc att gag cta act gac aaa gaa ggc gac gat gta aca     384
Tyr Lys Gln Gly Ile Glu Leu Thr Asp Lys Glu Gly Asp Asp Val Thr
        115                 120                 125 aac gat atg cta att gca ttt aaa gct agc att gac aaa cat atc tgg     432
Asn Asp Met Leu Ile Ala Phe Lys Ala Ser Ile Asp Lys His Ile Trp
    130                 135                 140 atg ttc aaa gca ttc ctt gga aaa gct cca tta gaa taa                  471
Met Phe Lys Ala Phe Leu Gly Lys Ala Pro Leu Glu
145                 150                 155

<210> SEQ ID NO 4
<211> LENGTH: 156
<212> TYPE: PRT
<213> ORGANISM: Listeria innocua

<400> SEQUENCE: 4

Met Lys Thr Ile Asn Ser Val Asp Thr Lys Glu Phe Leu Asn His Gln
```

```
            1               5                  10                  15
Val Ala Asn Leu Asn Val Phe Thr Val Lys Ile His Gln Ile His Trp
                    20                  25                  30

Tyr Met Arg Gly His Asn Phe Phe Thr Leu His Glu Lys Met Asp Asp
                35                  40                  45

Leu Tyr Ser Glu Phe Gly Glu Gln Met Asp Glu Val Ala Glu Arg Leu
            50                  55                  60

Leu Ala Ile Gly Gly Ser Pro Phe Ser Thr Leu Lys Glu Phe Leu Glu
65                  70                  75                  80

Asn Ala Ser Val Glu Glu Ala Pro Tyr Thr Lys Pro Lys Thr Met Asp
                    85                  90                  95

Gln Leu Met Glu Asp Leu Val Gly Thr Leu Glu Leu Leu Arg Asp Glu
                100                 105                 110

Tyr Lys Gln Gly Ile Glu Leu Thr Asp Lys Gly Asp Asp Val Thr
            115                 120                 125

Asn Asp Met Leu Ile Ala Phe Lys Ala Ser Ile Asp Lys His Ile Trp
130                 135                 140

Met Phe Lys Ala Phe Leu Gly Lys Ala Pro Leu Glu
145                 150                 155

<210> SEQ ID NO 5
<211> LENGTH: 36
<212> TYPE: DNA
<213> ORGANISM: Artificial Sequence
<220> FEATURE:
<223> OTHER INFORMATION: Nucleotide sequence encoding the amino acid
      sequence of carbon nanohorn binding peptide (CNHBP)
<220> FEATURE:
<221> NAME/KEY: CDS
<222> LOCATION: (1)..(36)

<400> SEQUENCE: 5 gac tac ttc tct tct ccg tac tac gaa cag ctg ttt                     36
Asp Tyr Phe Ser Ser Pro Tyr Tyr Glu Gln Leu Phe
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Synthetic Construct

<400> SEQUENCE: 6

Asp Tyr Phe Ser Ser Pro Tyr Tyr Glu Gln Leu Phe
1               5                   10

<210> SEQ ID NO 7
<211> LENGTH: 18
<212> TYPE: DNA
<213> ORGANISM: Artificial Sequence
<220> FEATURE:
<223> OTHER INFORMATION: Nucleotide sequence encoding the amino acid
      sequence of titanium binding peptide (TBP)
<220> FEATURE:
<221> NAME/KEY: CDS
<222> LOCATION: (1)..(18)

<400> SEQUENCE: 7 cgc aaa ctt ccg gat gcg                                             18
Arg Lys Leu Pro Asp Ala
1               5
```

```
<210> SEQ ID NO 8
<211> LENGTH: 6
<212> TYPE: PRT
<213> ORGANISM: Artificial Sequence
<220> FEATURE:
<223> OTHER INFORMATION: Synthetic Construct

<400> SEQUENCE: 8

Arg Lys Leu Pro Asp Ala
1               5

<210> SEQ ID NO 9
<211> LENGTH: 39
<212> TYPE: DNA
<213> ORGANISM: Artificial Sequence
<220> FEATURE:
<223> OTHER INFORMATION: Synthetic DNA

<400> SEQUENCE: 9
tatggactac ttctcttctc cgtactacga acagctgtt                          39

<210> SEQ ID NO 10
<211> LENGTH: 39
<212> TYPE: DNA
<213> ORGANISM: Artificial Sequence
<220> FEATURE:
<223> OTHER INFORMATION: Synthetic DNA

<400> SEQUENCE: 10
taaacagctg ttcgtagtac ggagaagaga agtagtcca                          39

<210> SEQ ID NO 11
<211> LENGTH: 26
<212> TYPE: DNA
<213> ORGANISM: Artificial Sequence
<220> FEATURE:
<223> OTHER INFORMATION: Primer

<400> SEQUENCE: 11
tttggatccg aattcgagct ccgtcg                                        26

<210> SEQ ID NO 12
<211> LENGTH: 50
<212> TYPE: DNA
<213> ORGANISM: Artificial Sequence
<220> FEATURE:
<223> OTHER INFORMATION: Primer

<400> SEQUENCE: 12
tttggatcct tacgcatccg gaagtttgcg catttctaat ggagcttttc              50

<210> SEQ ID NO 13
<211> LENGTH: 12
<212> TYPE: PRT
<213> ORGANISM: Artificial Sequence
<220> FEATURE:
<223> OTHER INFORMATION: Peptide capable of binding to a carbon material

<400> SEQUENCE: 13

His Ser Ser Tyr Trp Tyr Ala Phe Asn Asn Lys Thr
1               5                   10

<210> SEQ ID NO 14
<211> LENGTH: 7
<212> TYPE: PRT
<213> ORGANISM: Artificial Sequence
<220> FEATURE:
```

```
<223> OTHER INFORMATION: Peptide capable of binding to a carbon material

<400> SEQUENCE: 14

Tyr Asp Pro Phe His Ile Ile
1               5

<210> SEQ ID NO 15
<211> LENGTH: 19
<212> TYPE: PRT
<213> ORGANISM: Artificial Sequence
<220> FEATURE:
<223> OTHER INFORMATION: Peptide capable of binding to a metal material

<400> SEQUENCE: 15

Ser Ser Lys Lys Ser Gly Ser Tyr Ser Gly Ser Lys Gly Ser Lys Arg
1               5                   10                  15

Arg Ile Leu

<210> SEQ ID NO 16
<211> LENGTH: 12
<212> TYPE: PRT
<213> ORGANISM: Artificial Sequence
<220> FEATURE:
<223> OTHER INFORMATION: Peptide capable of binding to a metal material

<400> SEQUENCE: 16

Arg Lys Leu Pro Asp Ala Pro Gly Met His Thr Trp
1               5                   10

<210> SEQ ID NO 17
<211> LENGTH: 6
<212> TYPE: PRT
<213> ORGANISM: Artificial Sequence
<220> FEATURE:
<223> OTHER INFORMATION: Peptide capable of binding to a metal material

<400> SEQUENCE: 17

Arg Ala Leu Pro Asp Ala
1               5

<210> SEQ ID NO 18
<211> LENGTH: 12
<212> TYPE: PRT
<213> ORGANISM: Artificial Sequence
<220> FEATURE:
<223> OTHER INFORMATION: Peptide capable of binding to a silicon
      material

<400> SEQUENCE: 18

Met Ser Pro His Pro His Pro Arg His His His Thr
1               5                   10

<210> SEQ ID NO 19
<211> LENGTH: 9
<212> TYPE: PRT
<213> ORGANISM: Artificial Sequence
<220> FEATURE:
<223> OTHER INFORMATION: Peptide capable of binding to a silicon
      material

<400> SEQUENCE: 19

Arg Arg Arg Leu Ser Cys Arg Leu Leu
1               5

<210> SEQ ID NO 20
<211> LENGTH: 12
```

```
<212> TYPE: PRT
<213> ORGANISM: Artificial Sequence
<220> FEATURE:
<223> OTHER INFORMATION: Peptide capable of binding to a silicon
      material

<400> SEQUENCE: 20

Lys Pro Ser His His His His His Thr Gly Ala Asn
1               5                   10

<210> SEQ ID NO 21
<211> LENGTH: 35
<212> TYPE: PRT
<213> ORGANISM: Artificial Sequence
<220> FEATURE:
<223> OTHER INFORMATION: Fusion peptide (P1R5 peptide)

<400> SEQUENCE: 21

Ser Ser Lys Lys Ser Gly Ser Tyr Ser Gly Ser Lys Gly Ser Lys Arg
1               5                   10                  15

Arg Ile Leu Gly Gly Gly Gly His Ser Ser Tyr Trp Tyr Ala Phe Asn
            20                  25                  30

Asn Lys Thr
        35

<210> SEQ ID NO 22
<211> LENGTH: 33
<212> TYPE: DNA
<213> ORGANISM: Artificial Sequence
<220> FEATURE:
<223> OTHER INFORMATION: Primer

<400> SEQUENCE: 22
tttcatatgt atatctcctt cttaaagtta aac                              33

<210> SEQ ID NO 23
<211> LENGTH: 31
<212> TYPE: DNA
<213> ORGANISM: Artificial Sequence
<220> FEATURE:
<223> OTHER INFORMATION: Primer

<400> SEQUENCE: 23
tttcatatga tgaaaacaat caactcagta g                                31

<210> SEQ ID NO 24
<211> LENGTH: 63
<212> TYPE: DNA
<213> ORGANISM: Artificial Sequence
<220> FEATURE:
<223> OTHER INFORMATION: Primer

<400> SEQUENCE: 24
tttcatatgg actacttctc ttctccgtac tacgaacagc tgtttatggc aaactacaca   60
gtc                                                                63

<210> SEQ ID NO 25
<211> LENGTH: 51
<212> TYPE: DNA
<213> ORGANISM: Artificial Sequence
<220> FEATURE:
<223> OTHER INFORMATION: Primer

<400> SEQUENCE: 25
tttgaattct tacgcatccg gaagtttgcg catctcttgg atgtttccgt c            51
```

<210> SEQ ID NO 26
<211> LENGTH: 558
<212> TYPE: DNA
<213> ORGANISM: Artificial Sequence
<220> FEATURE:
<223> OTHER INFORMATION: Nucleotide sequence encoding an amino acid
      sequence of fusion protein
<220> FEATURE:
<221> NAME/KEY: CDS
<222> LOCATION: (1)..(558)

<400> SEQUENCE: 26

```
atg gac tac ttc tct tct ccg tac tac gaa cag ctg ttt atg gca aac        48
Met Asp Tyr Phe Ser Ser Pro Tyr Tyr Glu Gln Leu Phe Met Ala Asn
1               5                   10                  15 tac aca gtc cct gga atc aac gag aat gac gca aag cag ctt att gat        96
Tyr Thr Val Pro Gly Ile Asn Glu Asn Asp Ala Lys Gln Leu Ile Asp
            20                  25                  30 gga ctg cag gag cgt ctc acc gac tac aac gat ctt cac ctc atc ttg       144
Gly Leu Gln Glu Arg Leu Thr Asp Tyr Asn Asp Leu His Leu Ile Leu
        35                  40                  45 aag cac gtg cac tgg aac gtc act ggc ccc aac ttc att gct gtt cac       192
Lys His Val His Trp Asn Val Thr Gly Pro Asn Phe Ile Ala Val His
    50                  55                  60 gaa atg ctc gac cca cag gtt gac ctt gtt cgt ggc tat gct gac gaa       240
Glu Met Leu Asp Pro Gln Val Asp Leu Val Arg Gly Tyr Ala Asp Glu
65                  70                  75                  80 gtt gca gag cgc att tcc acc ctc gga ggc gca cca gtt gga acc cca       288
Val Ala Glu Arg Ile Ser Thr Leu Gly Gly Ala Pro Val Gly Thr Pro
                85                  90                  95 gaa ggc cac gtt gct gac cgc acc cca ctg caa tat gag cgc aat gcc       336
Glu Gly His Val Ala Asp Arg Thr Pro Leu Gln Tyr Glu Arg Asn Ala
            100                 105                 110 gga aat gtc caa gca cac ctc act gac ctc aat cgc gtg tac acc caa       384
Gly Asn Val Gln Ala His Leu Thr Asp Leu Asn Arg Val Tyr Thr Gln
        115                 120                 125 gtg ctg acc gga gtt cgc gag tcc atg gca tca gcc ggc cca gtg gat       432
Val Leu Thr Gly Val Arg Glu Ser Met Ala Ser Ala Gly Pro Val Asp
    130                 135                 140 cca gta act gaa gac atc tac atc agc cag gcc gcg gag ctg gag aaa       480
Pro Val Thr Glu Asp Ile Tyr Ile Ser Gln Ala Ala Glu Leu Glu Lys
145                 150                 155                 160 ttc cag tgg ttc atc cgc gca cac att gtt gat gta gac gga aac atc       528
Phe Gln Trp Phe Ile Arg Ala His Ile Val Asp Val Asp Gly Asn Ile
                165                 170                 175 caa gag atg cgc aaa ctt ccg gat gcg taa                               558
Gln Glu Met Arg Lys Leu Pro Asp Ala
            180                 185
```

<210> SEQ ID NO 27
<211> LENGTH: 185
<212> TYPE: PRT
<213> ORGANISM: Artificial Sequence
<220> FEATURE:
<223> OTHER INFORMATION: Synthetic Construct

<400> SEQUENCE: 27

```
Met Asp Tyr Phe Ser Ser Pro Tyr Tyr Glu Gln Leu Phe Met Ala Asn
1               5                   10                  15

Tyr Thr Val Pro Gly Ile Asn Glu Asn Asp Ala Lys Gln Leu Ile Asp
            20                  25                  30
```

```
Gly Leu Gln Glu Arg Leu Thr Asp Tyr Asn Asp Leu His Leu Ile Leu
             35                  40                  45

Lys His Val His Trp Asn Val Thr Gly Pro Asn Phe Ile Ala Val His
 50                  55                  60

Glu Met Leu Asp Pro Gln Val Asp Leu Val Arg Gly Tyr Ala Asp Glu
 65                  70                  75                  80

Val Ala Glu Arg Ile Ser Thr Leu Gly Gly Ala Pro Val Gly Thr Pro
                 85                  90                  95

Glu Gly His Val Ala Asp Arg Thr Pro Leu Gln Tyr Glu Arg Asn Ala
            100                 105                 110

Gly Asn Val Gln Ala His Leu Thr Asp Leu Asn Arg Val Tyr Thr Gln
        115                 120                 125

Val Leu Thr Gly Val Arg Glu Ser Met Ala Ser Ala Gly Pro Val Asp
130                 135                 140

Pro Val Thr Glu Asp Ile Tyr Ile Ser Gln Ala Ala Glu Leu Glu Lys
145                 150                 155                 160

Phe Gln Trp Phe Ile Arg Ala His Ile Val Asp Val Asp Gly Asn Ile
                165                 170                 175

Gln Glu Met Arg Lys Leu Pro Asp Ala
            180                 185

<210> SEQ ID NO 28
<211> LENGTH: 495
<212> TYPE: DNA
<213> ORGANISM: Corynebacterium glutamicum
<220> FEATURE:
<221> NAME/KEY: CDS
<222> LOCATION: (1)..(495)

<400> SEQUENCE: 28 atg gca aac tac aca gtc cct gga atc aac gag aat gac gca aag cag      48
Met Ala Asn Tyr Thr Val Pro Gly Ile Asn Glu Asn Asp Ala Lys Gln
 1               5                  10                  15 ctt att gat gga ctg cag gag cgt ctc acc gac tac aac gat ctt cac      96
Leu Ile Asp Gly Leu Gln Glu Arg Leu Thr Asp Tyr Asn Asp Leu His
             20                  25                  30 ctc atc ttg aag cac gtg cac tgg aac gtc act ggc ccc aac ttc att     144
Leu Ile Leu Lys His Val His Trp Asn Val Thr Gly Pro Asn Phe Ile
         35                  40                  45 gct gtt cac gaa atg ctc gac cca cag gtt gac ctt gtt cgt ggc tat     192
Ala Val His Glu Met Leu Asp Pro Gln Val Asp Leu Val Arg Gly Tyr
     50                  55                  60 gct gac gaa gtt gca gag cgc att tcc acc ctc gga ggc gca cca gtt     240
Ala Asp Glu Val Ala Glu Arg Ile Ser Thr Leu Gly Gly Ala Pro Val
 65                  70                  75                  80 gga acc cca gaa ggc cac gtt gct gac cgc acc cca ctg caa tat gag     288
Gly Thr Pro Glu Gly His Val Ala Asp Arg Thr Pro Leu Gln Tyr Glu
                 85                  90                  95 cgc aat gcc gga aat gtc caa gca cac ctc act gac ctc aat cgc gtg     336
Arg Asn Ala Gly Asn Val Gln Ala His Leu Thr Asp Leu Asn Arg Val
            100                 105                 110 tac acc caa gtg ctg acc gga gtt cgc gag tcc atg gca tca gcc ggc     384
Tyr Thr Gln Val Leu Thr Gly Val Arg Glu Ser Met Ala Ser Ala Gly
        115                 120                 125 cca gtg gat cca gta act gaa gac atc tac atc agc cag gcc gcg gag     432
Pro Val Asp Pro Val Thr Glu Asp Ile Tyr Ile Ser Gln Ala Ala Glu
130                 135                 140 ctg gag aaa ttc cag tgg ttc atc cgc gca cac att gtt gat gta gac     480
Leu Glu Lys Phe Gln Trp Phe Ile Arg Ala His Ile Val Asp Val Asp
145                 150                 155                 160
```

```
                    145                 150                 155                 160
gga aac atc caa gag                                                                          495
Gly Asn Ile Gln Glu
                165
```

<210> SEQ ID NO 29
<211> LENGTH: 165
<212> TYPE: PRT
<213> ORGANISM: Corynebacterium glutamicum

<400> SEQUENCE: 29

```
Met Ala Asn Tyr Thr Val Pro Gly Ile Asn Glu Asn Asp Ala Lys Gln
1               5                   10                  15

Leu Ile Asp Gly Leu Gln Glu Arg Leu Thr Asp Tyr Asn Asp Leu His
            20                  25                  30

Leu Ile Leu Lys His Val His Trp Asn Val Thr Gly Pro Asn Phe Ile
        35                  40                  45

Ala Val His Glu Met Leu Asp Pro Gln Val Asp Leu Val Arg Gly Tyr
    50                  55                  60

Ala Asp Glu Val Ala Glu Arg Ile Ser Thr Leu Gly Gly Ala Pro Val
65                  70                  75                  80

Gly Thr Pro Glu Gly His Val Ala Asp Arg Thr Pro Leu Gln Tyr Glu
                85                  90                  95

Arg Asn Ala Gly Asn Val Gln Ala His Leu Thr Asp Leu Asn Arg Val
            100                 105                 110

Tyr Thr Gln Val Leu Thr Gly Val Arg Glu Ser Met Ala Ser Ala Gly
        115                 120                 125

Pro Val Asp Pro Val Thr Glu Asp Ile Tyr Ile Ser Gln Ala Ala Glu
    130                 135                 140

Leu Glu Lys Phe Gln Trp Phe Ile Arg Ala His Ile Val Asp Val Asp
145                 150                 155                 160

Gly Asn Ile Gln Glu
                165
```

<210> SEQ ID NO 30
<211> LENGTH: 17
<212> TYPE: PRT
<213> ORGANISM: Artificial Sequence
<220> FEATURE:
<223> OTHER INFORMATION: Amino acid sequence of peptide of mineralizing
      zinc oxide

<400> SEQUENCE: 30

```
Glu Ala His Val Met His Lys Val Ala Pro Arg Pro Gly Gly Gly Ser
1               5                   10                  15

Cys
```

<210> SEQ ID NO 31
<211> LENGTH: 561
<212> TYPE: DNA
<213> ORGANISM: Artificial Sequence
<220> FEATURE:
<223> OTHER INFORMATION: Nucleotide sequence encoding an amino acid
      sequence of fusion protein
<220> FEATURE:
<221> NAME/KEY: CDS
<222> LOCATION: (1)..(561)

<400> SEQUENCE: 31

```
atg gac tac ttc tct tct ccg tac tac gaa cag ctg ttt atg aaa aca           48
Met Asp Tyr Phe Ser Ser Pro Tyr Tyr Glu Gln Leu Phe Met Lys Thr
```

```
            1               5                  10                 15
atc aac tca gta gac aca aag gaa ttt ttg aat cat caa gta gcg aat     96
Ile Asn Ser Val Asp Thr Lys Glu Phe Leu Asn His Gln Val Ala Asn
              20                  25                  30 tta aac gta ttc aca gta aaa att cat caa att cat tgg tat atg aga    144
Leu Asn Val Phe Thr Val Lys Ile His Gln Ile His Trp Tyr Met Arg
              35                  40                  45 ggc cac aac ttc ttc act tta cat gaa aaa atg gat gat tta tat agc    192
Gly His Asn Phe Phe Thr Leu His Glu Lys Met Asp Asp Leu Tyr Ser
 50                  55                  60 gaa ttc ggt gaa caa atg gat gaa gta gca gaa cgt tta ctt gcc att    240
Glu Phe Gly Glu Gln Met Asp Glu Val Ala Glu Arg Leu Leu Ala Ile
 65                  70                  75                  80 ggt gga agc cca ttc tcg act tta aaa gag ttt tta gaa aat gcg agt    288
Gly Gly Ser Pro Phe Ser Thr Leu Lys Glu Phe Leu Glu Asn Ala Ser
              85                  90                  95 gta gaa gaa gct cct tat aca aaa cct aaa act atg gat caa tta atg    336
Val Glu Glu Ala Pro Tyr Thr Lys Pro Lys Thr Met Asp Gln Leu Met
             100                 105                 110 gaa gac tta gtt ggt aca tta gaa tta ctt aga gac gaa tat aaa caa    384
Glu Asp Leu Val Gly Thr Leu Glu Leu Leu Arg Asp Glu Tyr Lys Gln
             115                 120                 125 ggc att gag cta act gac aaa gaa ggc gac gat gta aca aac gat atg    432
Gly Ile Glu Leu Thr Asp Lys Glu Gly Asp Asp Val Thr Asn Asp Met
             130                 135                 140 cta att gca ttt aaa gct agc att gac aaa cat atc tgg atg ttc aaa    480
Leu Ile Ala Phe Lys Ala Ser Ile Asp Lys His Ile Trp Met Phe Lys
145                 150                 155                 160 gca ttc ctt gga aaa gct cca tta gaa gaa gca cat gta atg cat aaa    528
Ala Phe Leu Gly Lys Ala Pro Leu Glu Glu Ala His Val Met His Lys
             165                 170                 175 gtt gct cca cgt cct ggt gga ggt agt tgt taa                        561
Val Ala Pro Arg Pro Gly Gly Gly Ser Cys
             180                 185
```

<210> SEQ ID NO 32
<211> LENGTH: 186
<212> TYPE: PRT
<213> ORGANISM: Artificial Sequence
<220> FEATURE:
<223> OTHER INFORMATION: Synthetic Construct

<400> SEQUENCE: 32

```
Met Asp Tyr Phe Ser Ser Pro Tyr Tyr Glu Gln Leu Phe Met Lys Thr
 1               5                  10                  15

Ile Asn Ser Val Asp Thr Lys Glu Phe Leu Asn His Gln Val Ala Asn
              20                  25                  30

Leu Asn Val Phe Thr Val Lys Ile His Gln Ile His Trp Tyr Met Arg
              35                  40                  45

Gly His Asn Phe Phe Thr Leu His Glu Lys Met Asp Asp Leu Tyr Ser
 50                  55                  60

Glu Phe Gly Glu Gln Met Asp Glu Val Ala Glu Arg Leu Leu Ala Ile
 65                  70                  75                  80

Gly Gly Ser Pro Phe Ser Thr Leu Lys Glu Phe Leu Glu Asn Ala Ser
              85                  90                  95

Val Glu Glu Ala Pro Tyr Thr Lys Pro Lys Thr Met Asp Gln Leu Met
             100                 105                 110

Glu Asp Leu Val Gly Thr Leu Glu Leu Leu Arg Asp Glu Tyr Lys Gln
             115                 120                 125
```

```
Gly Ile Glu Leu Thr Asp Lys Glu Gly Asp Asp Val Thr Asn Asp Met
    130                 135                 140

Leu Ile Ala Phe Lys Ala Ser Ile Asp Lys His Ile Trp Met Phe Lys
145                 150                 155                 160

Ala Phe Leu Gly Lys Ala Pro Leu Glu Glu Ala His Val Met His Lys
                165                 170                 175

Val Ala Pro Arg Pro Gly Gly Gly Ser Cys
            180                 185

<210> SEQ ID NO 33
<211> LENGTH: 80
<212> TYPE: DNA
<213> ORGANISM: Artificial Sequence
<220> FEATURE:
<223> OTHER INFORMATION: Primer

<400> SEQUENCE: 33
tttggatcct taacaactac ctccaccagg acgtggagca actttatgca ttacatgtgc    60
ttcttctaat ggagcttttc                                                80
```